(12) United States Patent
John et al.

(10) Patent No.: US 6,602,202 B2
(45) Date of Patent: Aug. 5, 2003

(54) SYSTEM AND METHODS FOR OBJECTIVE EVALUATION OF HEARING USING AUDITORY STEADY-STATE RESPONSES

(75) Inventors: Michael Sasha John, Toronto (CA); Terence W. Picton, Toronto (CA)

(73) Assignee: Baycrest Centre for Geriatric Care, Toronto ( * ) Notice: Subject to any disclaimer, the term of this patent is extended or adjusted under 35 U.S.C. 154(b) by 260 days.

(21) Appl. No.: 09/859,637

(22) Filed: May 18, 2001

(65) Prior Publication Data

US 2001/0049480 A1 Dec. 6, 2001

Related U.S. Application Data

(60) Provisional application No. 60/287,387, filed on May 1, 2001, provisional application No. 60/247,999, filed on Nov. 14, 2000, and provisional application No. 60/205,469, filed on May 19, 2000.

(51) Int. Cl.[7] .............................. A61B 5/04; A61B 5/12
(52) U.S. Cl. ..................... 600/559; 600/544; 73/585
(58) Field of Search ................................. 600/544, 559; 73/585

(56) References Cited

U.S. PATENT DOCUMENTS

| | | |
|---|---|---|
| 4,275,744 A | 6/1981 | Thornton et al. |
| 4,321,427 A | 3/1982 | Singh |
| 4,462,411 A | 7/1984 | Rickards |
| 4,556,069 A | 12/1985 | Dalton, Jr. et al. |
| 4,561,449 A | 12/1985 | Hu et al. |
| 4,901,353 A | 2/1990 | Widin |
| 4,913,160 A | 4/1990 | John |
| 4,953,112 A | 8/1990 | Widin et al. |
| 5,023,783 A | 6/1991 | Cohen et al. |

(List continued on next page.)

FOREIGN PATENT DOCUMENTS

| | | |
|---|---|---|
| WO | WO 97/04704 | 2/1997 |
| WO | WO 99/53839 | 10/1999 |

OTHER PUBLICATIONS

M.S. John and T.W. Picton, *Master: A Windows Program for Recording Multiple Auditory Steady–State Responses*, Computer Methods and Programs in Biomedicine, vol. 61, Feb. 2000, pp. 125–150.

(List continued on next page.)

*Primary Examiner*—Joseph Pelham
(74) *Attorney, Agent, or Firm*—Marshall, Gerstein & Borun

(57) ABSTRACT

This invention relates to an apparatus and method for assessing a subject's hearing by recording steady-state auditory evoked responses. The apparatus generates a steady-state auditory evoked potential stimulus, presents the stimulus to the subject, senses potentials while simultaneously presenting the stimulus and determines whether the sensed potentials contain responses to the stimulus. The stimulus may include an optimum vector combined amplitude modulation and frequency modulation signal adjusted to evoke responses with increased amplitudes, an independent amplitude modulation and frequency modulation signal and a signal whose envelope is modulated by an exponential modulation signal. The apparatus is also adapted to reduce noise in the sensed potentials by employing sample weighted averaging. The apparatus is also adapted to detect responses in the sensed potentials via the Phase weighted T-test or Phase zone technique. The apparatus may further perform a number of objective audiological tests including latency tests, AM/FM discrimination tests, rate sensitivity tests, aided hearing tests, depth sensitivity tests, supra-threshold tests and auditory threshold tests. The apparatus is further adapted to perform multi-modality testing in which more than one sensory modality of the subject is tested simultaneously.

57 Claims, 14 Drawing Sheets

U.S. PATENT DOCUMENTS

| | | | |
|---|---|---|---|
| 5,105,822 A | | 4/1992 | Stevens et al. |
| 5,230,344 A | | 7/1993 | Ozdamar et al. |
| 5,267,571 A | | 12/1993 | Zurek et al. |
| 5,282,475 A | | 2/1994 | Urbach et al. |
| 5,601,091 A | | 2/1997 | Dolphin |
| 5,697,379 A | | 12/1997 | Neely et al. |
| 5,699,809 A | | 12/1997 | Combs et al. |
| 5,792,073 A | * | 8/1998 | Keefe .......................... 600/559 |
| 5,825,894 A | | 10/1998 | Shennib |
| 5,954,667 A | | 9/1999 | Finkenzeller et al. |
| 5,999,856 A | | 12/1999 | Kennedy |
| 6,071,246 A | | 6/2000 | Sturzebecher et al. |
| 6,110,126 A | | 8/2000 | Zoth et al. |

OTHER PUBLICATIONS

M.S. John and T.W. Picton, *Human Auditory Steady–State Responses to Amplitude–Modulated Tones: Phase and Latency Measurements*, Hearing Research, vol. 141, Mar. 2000, pp. 57–79.

Terence W. Picton et al., *Objective evaluation of Aided Thresholds Using Auditory Steady–State Responses*, Journal of American Audiology, vol. 9, No. 5, 1998, pp. 315–331.

Jerrold H. Zar, *Circular Distributions: Hypothesis Testing*, Biostatistical Analysis, 3d, 1996, pp. 533–535, 601–605, 615–620.

Michael S. John et al., *Multiple Auditory Steady–State Responses (MASTER): Stimulus and Recording Parameters*, Augiology, vol. 37, 1998, pp. 58–82.

Fergus W. Cambell et al., *Estimation of Auditory Thresholds Using Evoked Potentials: A Clinical Screening Test*, Prog. Clin. Neurophysiol, vol. 2, 1977, pp. 68–78.

Robert Galambos et al., *A 40–Hz Auditory Potential Recorded From The Human Scalp*, Proc. Natl. Acad. Sci. USA, vol. 78, No. 4, 1981, pp. 2643–2647.

Robert Galambos et al., *Clinical Applications of The Auditory Brain Stem Response*, Otolaryngologic Clinics of North America, vol. 11, No. 3, 1978, pp. 709–722.

The Journal of the Acoustical Society of America, vol. 95, No. 5, Pr. 2, 1994, pp. 2842–2843.

Carol Schulman–Galambos et al., *Brain Stem Evoked Response Audiometry in Newborn Hearing Screening*, Arch Otolaryngol, vol. 105, 1979, pp. 86–90.

Gary Rance et al., *The Automated Prediction of Hearing Thresholds In Sleeping Subjects Using Auditory Steady–State Evoked Potentials*. Ear Hear. Oct. 16, 1995, (5), pp. 499–507.

Field W. Rickards et al., *Auditory Steady–State Evoked Potentials in Newborns*. British Journal of Audiology, Dec. 28, 1994, (6), pp. 327–337.

Ekkehard Sturzebecher et al., *Efficient Stimuli for Recording of the Amplitude Modulation Following Response*. Audiology, 2001, vol. 40, No. 2, pp. 63–68.

Lawrence T. Cohen et al., *A Comparison of Steady–State Evoked Potentials to Modulated Tones in Awake and Sleeping Humans*. Journal of Acoustical Society of America, Nov. 1991, vol. 90, No. 5, pp. 2469–2479.

Andrew Dimitrijevic et al., *Human Auditory Steady–State Responses to Tones Independently Modulated in Both Frequency and Amplitude*. Ear Hear, Apr. 2001, (2), pp. 100–111.

M. Sasha John et al., *Weighted Averaging of Steady–State Responses*. Clinical Neurophysiology, 2001, (112), pp. 555–562.

M. Sasha John et al., *Multiple Auditory Steady–State Responses to AM and FM Stimuli*, Audiology Neurootol, 2001, vol. 6, pp. 12–27.

* cited by examiner

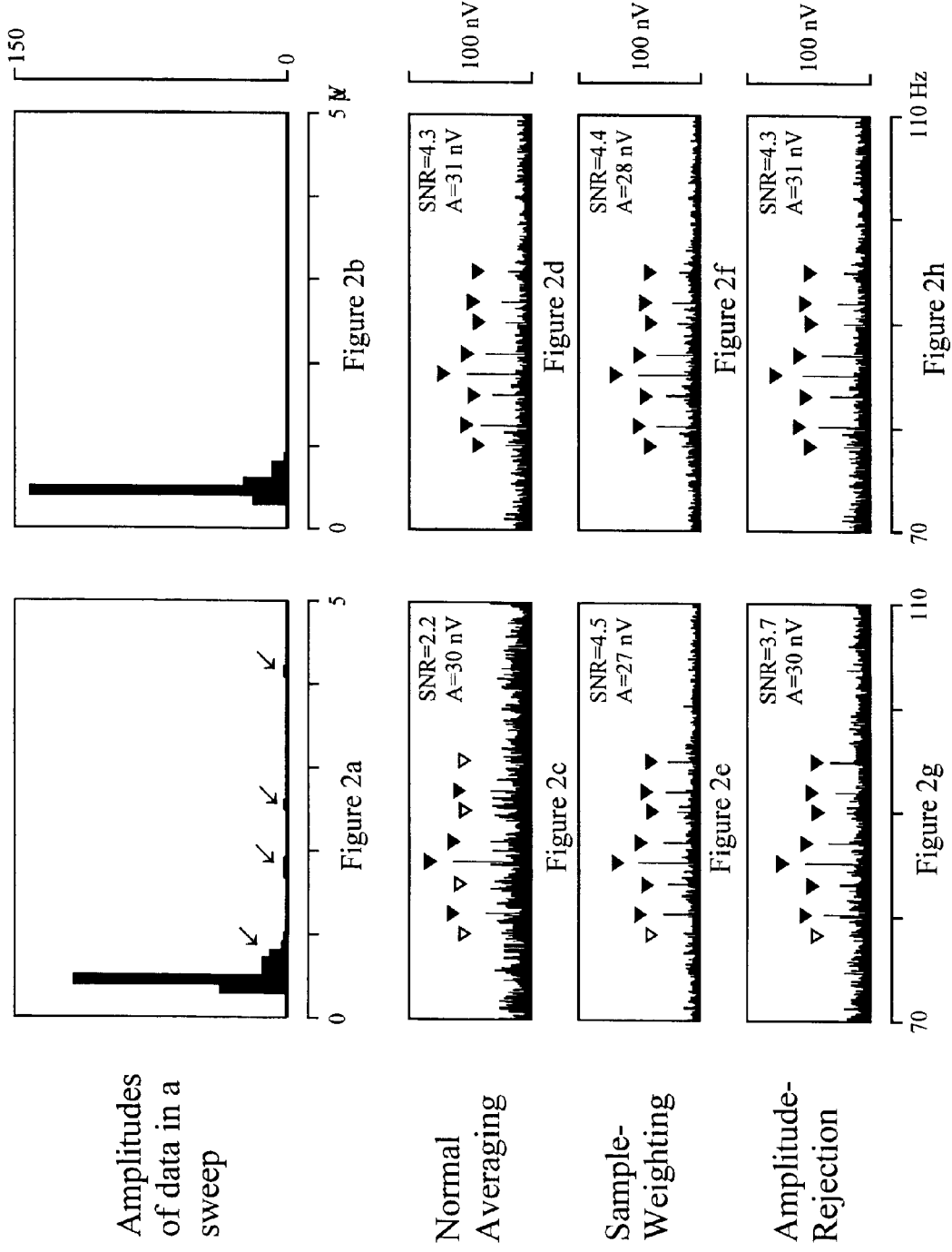

F=2.19; df 2,32; p=0.13
actual phase = 87 degrees t=2.29; df 15; p=0.02
expected phase = 104 degrees

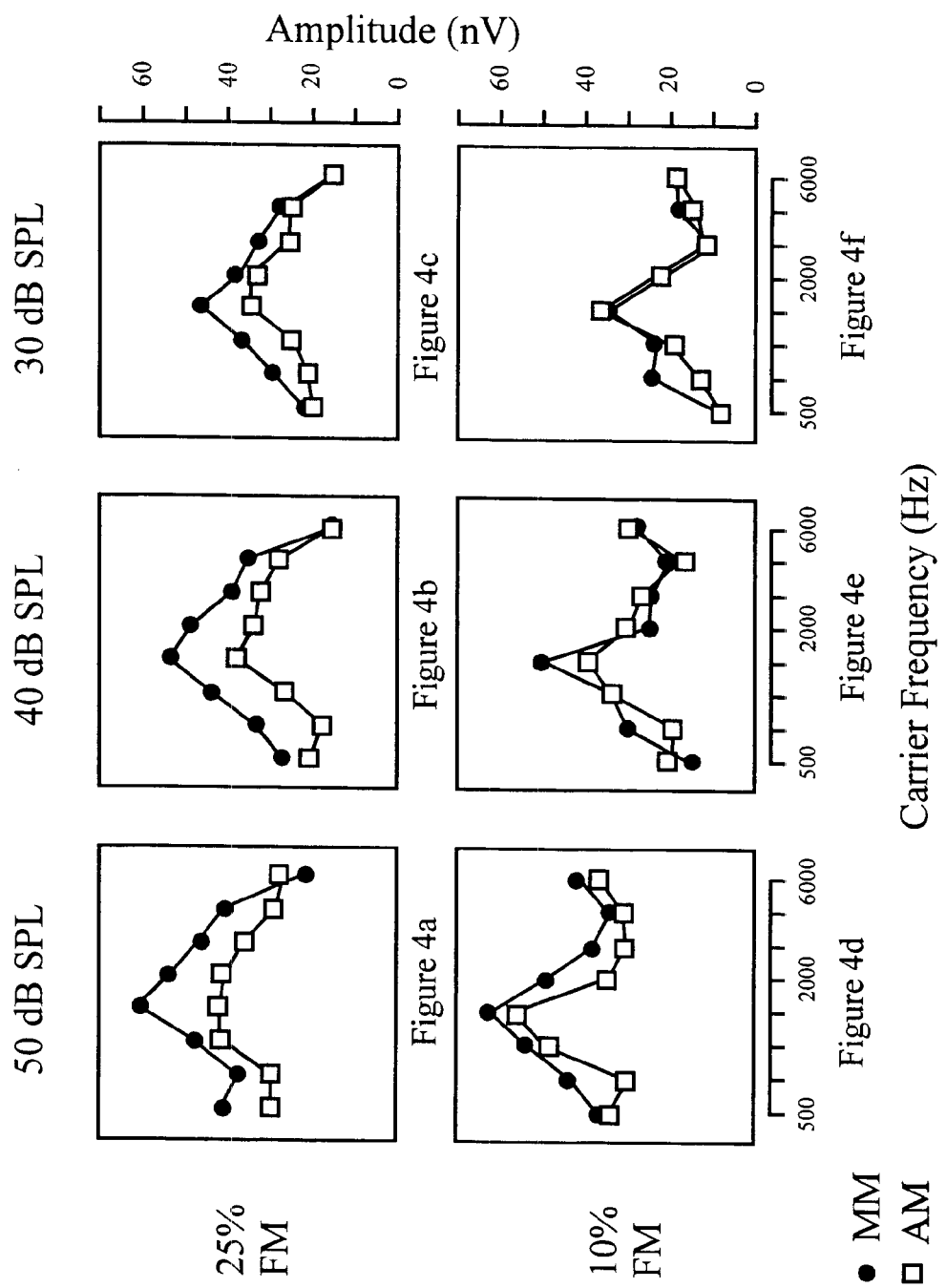

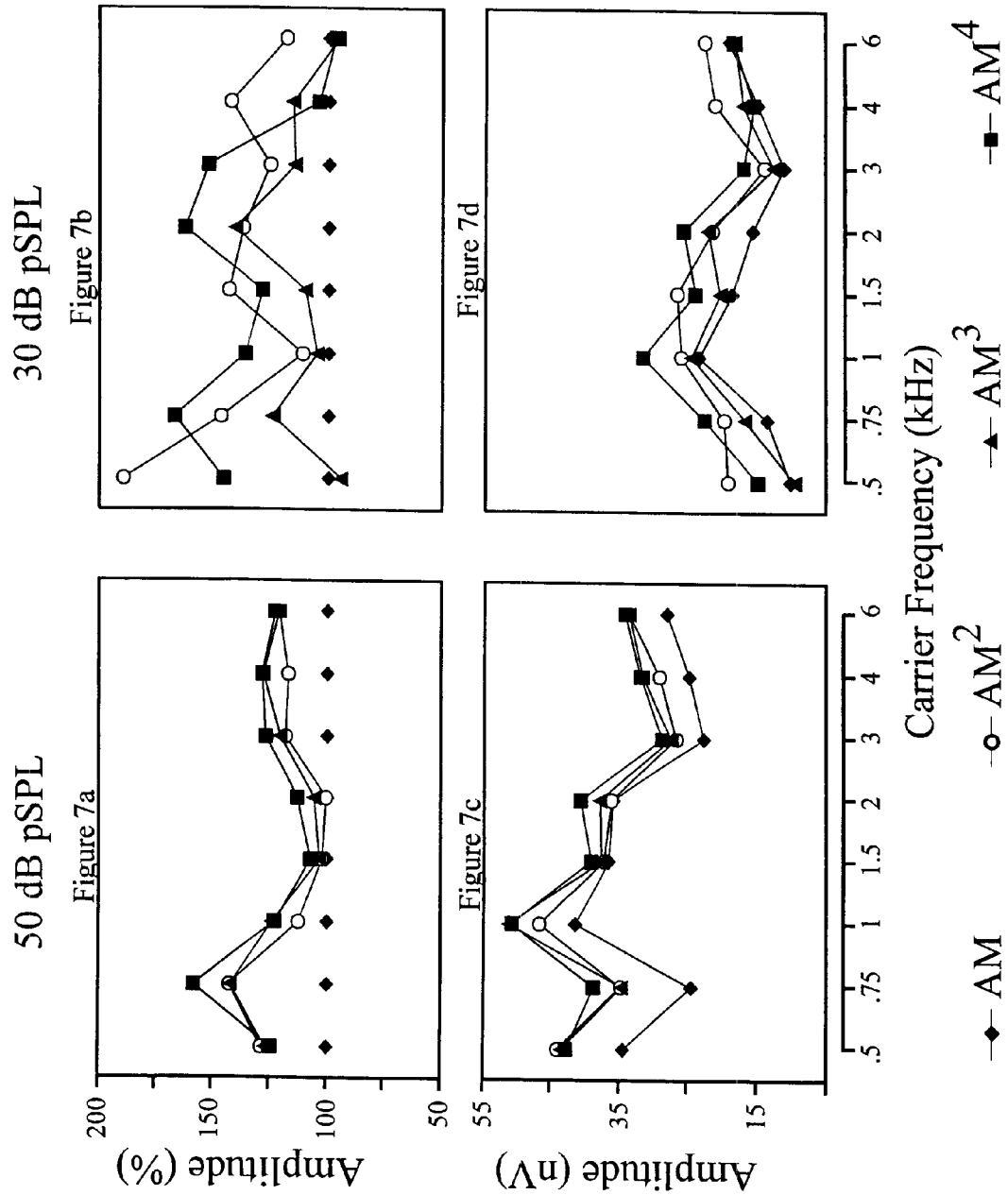

SYSTEM AND METHODS FOR OBJECTIVE EVALUATION OF HEARING USING AUDITORY STEADY-STATE RESPONSES

This application claims the benefit of Provisional Applications Ser. No. 60/205,469, filed May 19, 2000, Ser. No. 60/247,999, filed Nov. 14, 2000 and Ser. No. 60/287,387, filed May 1, 2001.

FIELD OF THE INVENTION

This invention is in the field of auditory assessment and relates to the identification and evaluation of hearing impairment. More particularly, the invention describes a system and method for objectively evaluating an individual's hearing abilities by recording auditory steady-state responses.

BACKGROUND OF THE INVENTION

Hearing-impairment is a significant health problem, particularly at the two ends of the human life span. Approximately one in a thousand newborn infants and more than a quarter of adults over the age of 65 have a significant hearing loss. In the case of infants, early detection of hearing loss is necessary to ensure that appropriate treatment is provided at an early stage and that the infant can develop normal speech and language. The detection of a hearing-impairment requires a measurement of how well someone can hear sound (i.e. audiometry).

Conventional audiometry is performed by having a subject respond to acoustic stimuli by pressing a button, saying "yes", or repeating words that may be presented in the stimulus. These tests are subjective in nature. Audiometry allows an audiologist to determine the auditory threshold of the subject, which is defined as the lowest intensity at which a sound can be heard. The audiologist evaluates the auditory threshold of a subject by using a stimulus that most commonly consists of a pure tone. The stimulus is presented via earphones, headphones, free field speakers or bone conduction transducers. The results are presented as an audiogram which shows auditory thresholds for tones of different frequencies. The audiogram is helpful for diagnosing the type of hearing loss a subject may have. The audiogram can also be used to fit a hearing aid and adjust the level of amplification of the hearing aid for subjects who require hearing aids.

Audiometry may also involve subjective testing at supra-threshold intensities to determine how well the subject's auditory system discriminates between different sounds (such as speech) presented at intensities at which they normally occur. The audiologist will therefore determine how many simple words a subject can accurately recognize at different intensities with and without different amounts of background noise. The audiologist may also conduct tests which measure how well the subject can discriminate changes in the intensity or frequency of a sound or how rapidly these changes occur.

Conventional audiometry cannot be performed if the subject is an infant, young child or cognitively impaired adult. In these cases, objective tests of hearing are necessary in which the subject does not have to make a conscious response. Objective audiometry is essential for detecting hearing impairment in infants or elderly patients as well as for evaluating functional hearing losses. Furthermore, few objective tests have been developed for supra-threshold tests of speech, frequency, or intensity discrimination.

One form of objective audiometry uses auditory evoked potentials. Auditory evoked potential testing consists of presenting the subject with an acoustic stimulus and simultaneously or concurrently sensing (i.e. recording) potentials from the subject. The sensed potentials are the subject's electroencephalogram (EEG) which contain the subject's response to the stimulus if the subject's auditory system has processed the stimulus. These potentials are analyzed to determine whether they contain a response to the acoustic stimulus or not. Auditory evoked potentials have been used to determine auditory thresholds and hearing at specific frequencies.

One particular class of auditory evoked potentials is steady-state evoked potentials (SSAEPs). The stimulus for the SSAEP consists of a carrier signal, which is usually a sinusoid, that is amplitude modulated by a modulation signal which is also usually a sinusoid. The SSAEP stimulus is presented to the subject while simultaneously recording the subject's EEG. If the auditory system of the subject responded to the SSAEP stimulus, then a corresponding steady-state sinusoidal signal should exist in the recorded EEG. The signal should have a frequency that is the same as the frequency of the modulation signal (i.e. modulation frequency). The presence of such a corresponding signal in the EEG is indicative of a response to the SSAEP stimulus. Alternatively, the phase of the carrier signal may be frequency modulated instead of or in addition to amplitude modulation to create the SSAEP stimulus.

The SSAEP stimulus is sufficiently frequency-specific to allow a particular part of the auditory system to be tested. Furthermore, the SSAEP stimulus is less liable to be affected by distortion in free-field speakers or hearing aids. Typical modulation frequencies which are used in SSAEP stimuli are between 30 to 50 Hz or 75 to 110 Hz. The latter range may be particularly useful for audiometry because at these rates, the SSAEP responses are not significantly affected by sleep and can be reliably recorded in infants. Furthermore, SSAEP responses at these rates result in audiometric threshold estimates that are well correlated with behavioral thresholds to pure tone stimuli. In SSAEP testing, the presence or absence of an SSAEP response to an SSAEP stimulus can be determined using several statistical techniques.

However, objective audiometry employing SSAEP testing is time-consuming because the amplitude of the SSAEP response is quite small compared to the background noise which is the subject's ongoing brain activity (i.e. EEG) while the test is being conducted. The SSAEP response thus has a small signal-to-noise ratio (SNR) which makes it difficult to detect the SSAEP response in a short time period. One technique to reduce SSAEP testing time is to use a multiple SSAEP stimulus which combines several SSAEP test signals (i.e. where a test signal is meant to mean one SSAEP stimulus). The potentials sensed from the subject during the presentation of the multiple SSAEP stimulus contains a linear superposition of SSAEP responses to each SSAEP test signal in the multiple SSAEP stimulus. This makes it possible to record the SSAEP responses to multiple (e.g., four or eight) stimuli in the same time that it takes to record the response to a single stimulus. Therefore, this technique results in a reduction of test time since the SSAEP responses to several SSAEP test signals may be detected concurrently. However, the SNR for each SSAEP response is still small and the testing time for recording the response to a single SSAEP stimulus has not been reduced. To reduce the SSAEP test time techniques are required to either increase the amplitude of the SSAEP response and/or decrease the amplitude of the noise that is recorded along with the SSAEP response. A more sensitive statistical method that can detect SSAEP responses with small SNRs would also be useful.

While objective testing identifies that a subject has a hearing loss, the next step is usually to treat the subject by providing them with a hearing aid. However, if the subject is an infant, a method is required to objectively adjust the hearing aid since this cannot be done with conventional subjective methods. Some objective methods have been developed such as determining the real-ear insertion gain when a hearing aid is in place. However, this method is only useful if one knows the actual unaided audiometric thresholds of the subject so that the hearing aid can be adjusted to match prescriptive targets. Furthermore, placement of a probe-tube in an infant can be challenging. There have also been methods based on click evoked auditory evoked potentials (i.e. wave V of the click-evoked ABR) but the stimuli used in these methods are restricted to certain frequency ranges and do not test the ability of the hearing aid to process continuous signals like speech. Accordingly, there still remains a need for an objective method to measure the benefits of a hearing aid in patients where behavioral thresholds and real-ear measurements are difficult to obtain.

SUMMARY OF THE INVENTION

The present invention is an apparatus for recording SSAEP responses and a set of methods for using the apparatus to test various aspects of a subject's auditory system. The apparatus comprises hardware to present SSAEP stimuli, to acquire EEG data while simultaneously presenting the SSAEP stimuli, and to analyze the EEG data to detect the presence of SSAEP responses. The apparatus further comprises software to enable the creation and presentation of the SSAEP stimuli, the acquisition of the EEG data (i.e. electrophysiological potentials) and the analysis of the EEG data. The software further enables displaying the results of ongoing testing and the final results of the test as well as the storage of the test results for subsequent viewing and/or analysis.

The present invention also includes software adapted to effect noise reduction algorithms which may include sample weighted averaging. The software is also adapted to effect statistical tests that are used to detect the SSAEP responses to the SSAEP stimuli. These statistical tests may include the phase weighted t-test, the phase zone technique and the modified Rayleigh test of circular uniformity (MRC).

The present invention also uses particular types of SSAEP stimuli to increase the amplitude of the resulting SSAEP responses. These SSAEP stimuli may include a combined amplitude modulation and frequency modulation signal in which the phase of the frequency modulated signal is adjusted relative to the phase of the amplitude modulated. These SSAEP stimuli may also include using an exponential modulation signal. The present invention also uses an SSAEP stimulus consisting of an independent amplitude modulation signal and frequency modulation signal wherein the AM modulation rate is different than the FM modulation rate. This stimulus evokes two SSAEP responses that can be independently analyzed.

In another aspect of the invention, these SSAEP stimuli can be used for a variety of objective tests such as determining audiometric thresholds and testing the aided and unaided hearing of a subject. The present invention further comprises several other audiometric protocols including latency tests, AM/FM discrimination tests, rate sensitivity tests, aided hearing tests, depth sensitivity tests and suprathreshold tests.

The present invention further comprises databases of normative data which can be used to construct SSAEP stimuli, detect SSAEP responses and determine whether detected SSAEP responses are indicative of normal or abnormal hearing. The databases contain data which are grouped by subject characteristics such as age, sex and state over a variety of stimulus characteristics such as type of SSAEP stimulus, the type of modulation (amplitude versus frequency), the modulation rates and modulation depth. The database also preferably contains data about SSAEP response characteristics such as latency and ratio of amplitudes of SSAEP responses to amplitude modulated and frequency modulated SSAEP stimuli.

In an alternative embodiment, the apparatus is adapted to perform multi-modality testing in which more than one sensory modality (i.e. vision and audition) of the subject is tested simultaneously.

The invention comprises a method of testing the hearing of a subject comprising the steps of:
  (a) selecting at least one test signal;
  (b) modulating at least one of the amplitude and frequency of the at least one test signal by an exponential modulation signal to produce at least one modulated test signal;
  (c) transducing the at least one modulated test signal to create an acoustic stimulus and presenting the acoustic stimulus to the subject;
  (d) sensing potentials from the subject while substantially simultaneously presenting the acoustic stimulus to the subject; and,
  (e) analyzing the potentials to determine whether the potentials comprise data indicative of the presence of at least one steady-state response to the acoustic stimulus.

The invention further comprises testing the hearing of a subject comprising the steps of:
  (a) creating an optimum-vector mixed modulation test signal comprising at least one signal having an amplitude modulated component with a first phase and a frequency modulated component with a second phase wherein the second phase is adjusted relative to the first phase to evoke an increased response from the subject;
  (b) transducing the test signal to create an acoustic stimulus and presenting the acoustic stimulus to the subject;
  (c) sensing potentials from the subject while substantially simultaneously presenting the acoustic stimulus to the subject; and,
  (d) analyzing the potentials to determine whether the potentials comprise data indicative of the presence of at least one steady-state response to the acoustic stimulus.

In another aspect, the invention comprises a method for testing the hearing of a subject comprising the steps of:
  (a) creating a test signal comprising at least one independent amplitude modulated and frequency modulated signal having an amplitude modulated component and a frequency modulated component, wherein the amplitude modulated component comprises a first modulation frequency and a first carrier frequency and the frequency modulated component comprises a second modulation frequency and a second carrier frequency wherein the first modulation frequency is substantially different from the second modulation frequency and the first carrier frequency is substantially similar to the second carrier frequency;
  (b) transducing the test signal to create an acoustic stimulus and presenting the acoustic stimulus to the subject;

(c) sensing potentials from the subject while substantially simultaneously presenting the acoustic stimulus to the subject; and, (d) analyzing the potentials to determine whether the potentials comprise data indicative of a steady-state response to each amplitude modulated component and a steady-state response to each frequency modulated component.

In another aspect, the invention comprises an apparatus for testing the hearing of a subject, wherein the apparatus comprises:

(a) a signal creator adapted to create a test signal comprising at least one combined amplitude modulated and frequency modulated signal having an amplitude modulated component with a first phase and a frequency modulated component with a second phase wherein the signal creator comprises means for adjusting the second phase relative to the first phase;

(b) a transducer electrically coupled to the processor and adapted to transduce the test signal to create an acoustic stimulus and present the acoustic stimulus to the subject;

(c) a sensor adapted to sense potentials from the subject while the acoustic stimulus is substantially simultaneously presented to the subject; and, (d) a processor electrically coupled to the sensor and adapted to receive the potentials and analyze the potentials to determine if the potentials comprise data indicative of at least one response to the acoustic stimulus.

In another aspect, the invention comprises a method of analyzing potentials to determine whether the potentials comprise data indicative of the presence of at least one steady-state response to a steady-state evoked potential stimulus. The method comprises the steps of:

(a) presenting an evoked potential stimulus to a subject;

(b) sensing potentials from the subject while substantially simultaneously presenting the stimulus to the subject to obtain a plurality of data points;

(c) transforming the plurality of data points into a second plurality of data points;

(d) biasing the second plurality of data points with an expected phase value to obtain a plurality of biased data points; and, (e) applying a statistical test to the plurality of biased data points to detect the response.

The invention further comprises a method of detecting a response to an evoked potential stimulus comprising the steps of:

(a) presenting an evoked potential stimulus to a subject;

(b) sensing potentials from the subject while substantially simultaneously presenting the stimulus to the subject to obtain a plurality of data points; and, (c) calculating phase values for the plurality of data points, wherein, a response is detected if an adequate number of the calculated phase values fall within a predetermined phase value range.

The invention further comprises an apparatus for testing the hearing of a subject, wherein the apparatus comprises:

(a) a signal creator adapted to create a test signal;

(b) a transducer electrically coupled to the signal creator and adapted to transduce the test signal to create an acoustic stimulus and present the acoustic stimulus to the subject;

(c) a sensor adapted to sense potentials from the subject while the acoustic stimulus is substantially simultaneously presented to the subject; and, (d) a processor electrically coupled to the sensor and adapted to receive the potentials and analyze the potentials to determine if the potentials comprise data indicative of at least one response to the acoustic stimulus;

wherein the analysis involves biasing the potentials based on an expected phase value. The apparatus further comprises a database of expected phase value data correlated to subject characteristics and stimulus characteristics.

In yet another aspect, the invention comprises a method of noise reduction for a plurality of data points which are obtained during steady-state evoked potential testing, wherein the plurality of data points comprise at least one signal and noise and wherein said method comprises the steps of:

(a) obtaining said plurality of data points;

(b) separating said plurality of data points into a plurality of epochs; and, (c) applying an adaptive noise reduction method to each epoch.

In another aspect, the invention comprises a method of objectively testing the hearing of a subject comprising the steps of:

(a) selecting an auditory test;

(b) creating an appropriate test signal comprising at least one component for the auditory test;

(c) transducing the test signal to create a stimulus and presenting said stimulus to the subject;

(d) sensing potentials from the subject while substantially simultaneously presenting the stimulus to the subject; and, (e) analyzing the potentials to detect at least one response.

In another aspect, the invention further comprises an apparatus for objectively testing the hearing of a subject, wherein the apparatus comprises:

(a) a selector adapted for selecting an auditory test to perform on the subject;

(b) a signal creator electrically coupled to the selector and adapted to create an appropriate test signal comprising at least one component for the test;

(c) a transducer electrically coupled to the signal creator and adapted to transduce the test signal to create an acoustic stimulus and present the acoustic stimulus to the subject;

(d) a sensor adapted to sense potentials from the subject while the acoustic stimulus is substantially simultaneously presented to the subject;

(e) a processor electrically coupled to the sensor and adapted to receive the potentials and analyze the potentials to determine if the potentials comprise data indicative of at least one response to the acoustic stimulus; and, (f) a programmable hearing aid coupled to said processor, wherein, the programmable hearing aid comprises a plurality of programmable gain factors for different frequency regions and at least one programmable filter slope.

In an alternative embodiment, the invention comprises a method of testing at least two senses of a subject, wherein the method comprises the steps of:

(a) selecting a first steady-state test signal to test a first sensory modality;

(b) transducing the first steady-state test signal to create a first stimulus and presenting the first stimulus to the subject;
(c) selecting a second steady-state test signal to test a second sensory modality;
(d) transducing the second steady-state test signal to create a second stimulus and presenting the second stimulus to the subject;
(e) sensing potentials while substantially simultaneously presenting both stimuli to the subject; and,
(f) analyzing the potentials to determine whether the potentials comprise data indicative of at least one steady-state response to the stimuli.

In an alternative embodiment, the invention further comprises an apparatus for testing at least two senses of a subject, wherein the apparatus comprises:
(a) a signal creator adapted to create a first steady-state test signal and a second steady-state test signal;
(b) a first transducer electrically coupled to the selector and adapted to transduce the first test signal to create a first stimulus and present the first stimulus to the subject;
(c) a second transducer electrically coupled to the selector and adapted to transduce the second test signal to create a second stimulus and present the second stimulus to the subject;
(d) a first sensor adapted to sense first potentials from the subject while the first stimulus is substantially simultaneously presented to the subject;
(e) a second sensor adapted to sense second potentials from the subject while the second stimulus is substantially simultaneously presented to the subject;
(f) a processor electrically coupled to the first sensor and adapted to receive the first potentials and analyze the first potentials to determine if the first potentials comprise data indicative of at least one response to the first stimulus; and,
(g) the processor, electrically coupled to the second sensor and adapted to receive the second potentials and analyze the second potentials to determine if the second potentials comprise data indicative of at least one response to the second stimulus,
wherein, each stimulus is presented substantially simultaneously.

Further objects and advantages of the invention will appear from the following description, taken together with the accompanying drawings.

BRIEF DESCRIPTION OF THE DRAWINGS

For a better understanding of the present invention and to show more clearly how it may be carried into effect, reference will now be made, by way of example, to the accompanying drawings which show a preferred embodiment of the present invention and in which:

FIG. 2a is a histogram of EEG amplitudes during a noisy recording session;

FIG. 2b is a histogram of EEG amplitudes during a quiet recording session;

FIG. 2c is the amplitude spectrum of the result of performing normal time averaging on the EEG data shown in FIG. 2a;

FIG. 2d is the amplitude spectrum of the result of performing normal time averaging on the EEG data shown in FIG. 2b;

FIG. 2e is the amplitude spectrum of the result of performing sample weighted averaging on the EEG data shown in FIG. 2a;

FIG. 2f is the amplitude spectrum of the result of performing sample weighted averaging on the EEG data shown in FIG. 2b;

FIG. 2g is the amplitude spectrum of the result of performing amplitude rejection on the EEG data shown in FIG. 2a and then performing normal time averaging;

FIG. 2h is the amplitude spectrum of the result of performing amplitude rejection on the EEG data shown in FIG. 2b and then performing normal time averaging;

FIG. 3b is a plot of the results of the phase weighted t-test for the same set of data shown in FIG. 3a;

FIG. 4a is a graph of SSAEP response amplitudes to an MM SSAEP stimulus and an AM SSAEP stimulus for a 50 dB SPL stimulus intensity and a frequency modulation depth of 25%;

FIG. 4b is a graph of SSAEP response amplitudes to an MM SSAEP stimulus and an AM SSAEP stimulus for a 40 dB SPL stimulus intensity and a frequency modulation depth of 25%;

FIG. 4c is a graph of SSAEP response amplitudes to an MM SSAEP stimulus and an AM SSAEP stimulus for a 30 dB SPL stimulus intensity and a frequency modulation depth of 25%;

FIG. 4d is a graph of SSAEP response amplitudes to an MM SSAEP stimulus and an AM SSAEP stimulus for a 50 dB SPL stimulus intensity and a frequency modulation depth of 10%;

FIG. 4e is a graph of SSAEP response amplitudes to an MM SSAEP stimulus and an AM SSAEP stimulus for a 40 dB SPL stimulus intensity and a frequency modulation depth of 10%;

FIG. 4f is a graph of SSAEP response amplitudes to a MM SSAEP stimulus and an AM SSAEP stimulus for a 30 dB SPL stimulus intensity and a frequency modulation depth of 10%;

FIG. 6a is the amplitude spectrum of the SSAEP response to an AM SSAEP stimulus, an FM SSAEP stimulus and an IAFM SSAEP stimulus;

FIG. 6b is a group of polar plots showing the detection of the SSAEP responses shown in FIG. 6a;

FIG. 7a is a graph of test results showing percent increase in SSAEP responses when using an exponential modulation signal in the SSAEP stimulus as compared to an AM SSAEP stimulus for a stimulus intensity of 50 dB pSPL;

FIG. 7b is a graph of test results showing percent increase in SSAEP responses when using an exponential modulation signal in the SSAEP stimulus as compared to an AM SSAEP stimulus for a stimulus intensity of 30 dB pSPL;

FIG. 7c is a graph of test results showing amplitudes of SSAEP responses when using an exponential modulation signal in the SSAEP stimulus as compared to an AM SSAEP stimulus for a stimulus intensity of 50 dB pSPL;

FIG. 7d is a graph of test results showing amplitudes of SSAEP responses when using an exponential modulation signal in the SSAEP stimulus as compared to an AM SSAEP stimulus for a stimulus intensity of 30 dB pSPL;

DETAILED DESCRIPTION OF THE INVENTION

The present invention provides an apparatus for recording steady-state evoked potentials and a set of methods for using the apparatus to test various aspects of a subject's hearing. The basic hardware and software components of the apparatus will be discussed first. Noise reduction methods will be discussed next followed by response detection. Test signals which can be used for SSAEPs will then be discussed. Finally, protocols for objective audiometric testing based on SSAEP stimuli will be discussed.

Hardware and Software Components of the Invention

Figure 1A:
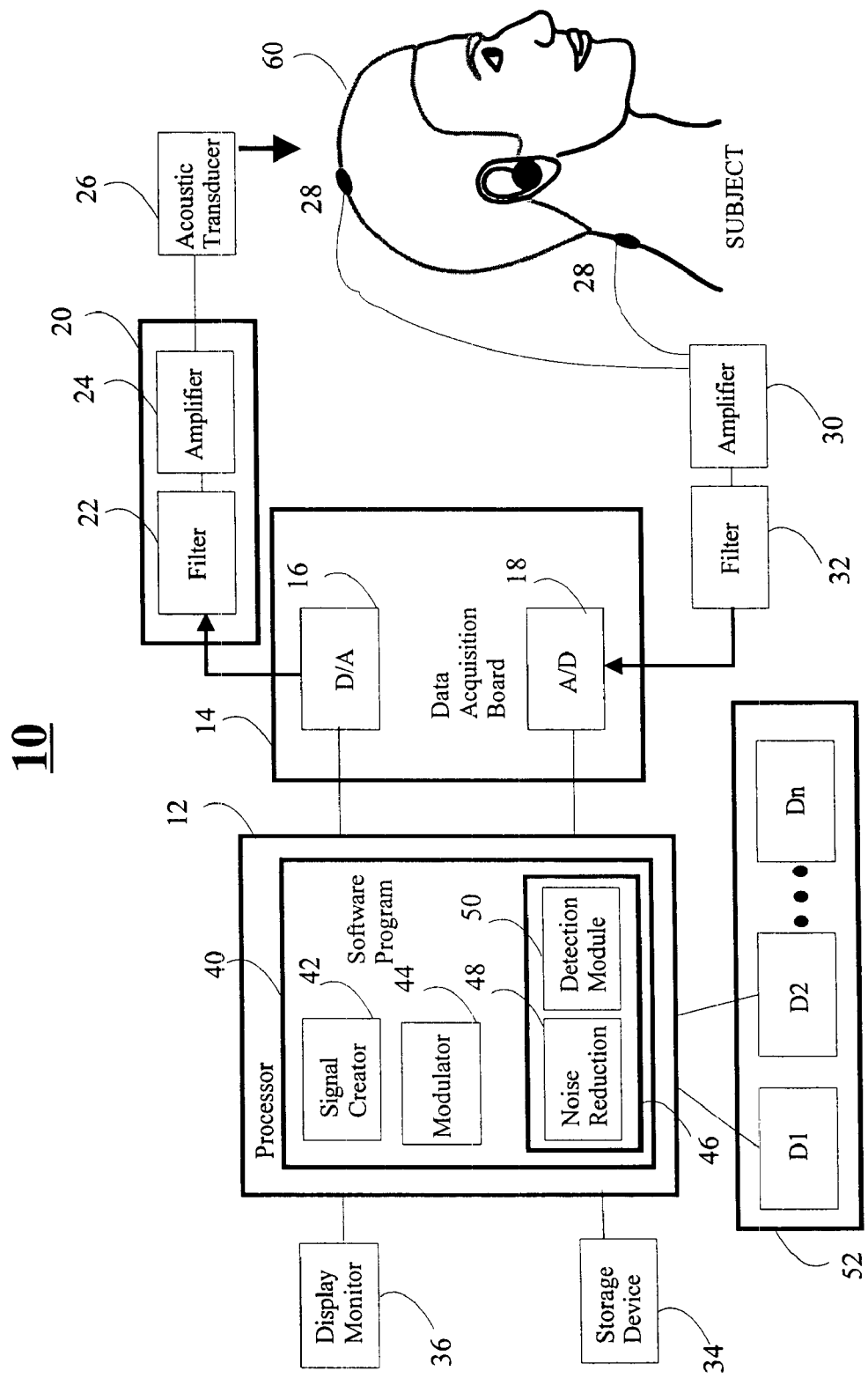
FIG. 1a is a schematic of an embodiment of the apparatus of the present invention.

Referring to FIG. 1a, the objective audiometric test apparatus 10 includes a processor 12, a data acquisition board 14 having a digital to analog converter (DAC) 16 and an analog to digital converter (ADC) 18, an audiometer 20 having a filter 22 and an amplifier 24, a transducer 26, a sensor 28, a second amplifier 30, a second filter 32, a master database 52 having a plurality of databases D1, D2, to Dn, a storage device 34 and a display monitor 36. The processor 12 is suitably programmed with a software program 40 comprising a signal creator module 42, a modulator module 44 and an analysis module 46 having a noise reduction module 48 and a detection module 50.

A personal computer, for example a Pentium 750 running Windows 98, may provide the processor 12, storage device 34 and display monitor 36. The software program 40 is run on the personal computer and the master database 52 along with the plurality of databases D1 to Dn can be stored in the memory of the personal computer and can communicate with the software program. Alternatively, these components may be effected on a laptop, a handheld computing device, such as a palmtop, or a dedicated electronics device.

The objective audiometric test apparatus 10 can be used to assess the auditory system of a subject 60 by presenting SSAEP stimuli to the subject 60. While the stimulus is being presented, the objective audiometric test apparatus 10 records sensed potentials (i.e. EEG data) and amplifies the EEG data. This is done while substantially simultaneously presenting the SSAEP stimuli to the subject 60. The EEG data is then processed and statistically evaluated to determine if the recorded EEG data contains SSAEP responses. For example, data processing may show the responses that are statistically significantly different than the background EEG noise levels. The design of the objective audiometric test apparatus 10 follows clear principles concerning the generation of the acoustic stimuli, the acquisition of artifact-free data, the analysis of EEG data in the frequency-domain and the objective detection of SSAEP responses in noise.

The processor 12 may be any modern processor such as a Pentium 750. The data acquisition board 14 is a commercial data acquisition board (AT-MIO-16E-10) available from National Instruments. Alternatively, another data acquisition board with a suitable number of input and output channels may be used. The data acquisition board 14 allows for the output of data via the DAC 16 as well as the input of data via the ADC 18.

The output from the DAC 16 is sent to the audiometer 20 which may also be under the control of the processor 12. The audiometer 20 acts to condition the stimulus which is presented to the subject 60 via the filter 22 and the amplifier 24. Rather than using the audiometer 20, functionally similar amplifying/attenuating and filtering hardware can be incorporated into the audiometric test apparatus 10 to control the intensity and frequency content of the stimulus that will be presented to the subject 60.

The SSAEP stimulus is presented to the subject 60 via the transducer 26 which may be a pair of speakers, headphones or at least one insert earphone. The insert earphones may be earphones designed by Etymotics Research. The transducer 26 allows the SSAEP stimulus to be presented to the left and/or right ears of the subject 60. The stimuli may also be presented using free-field speakers, bone conduction vibrators or other acoustic transducers.

While the stimulus is being presented to the subject 60, the EEG is substantially simultaneously sensed from the subject 60 using the sensor 28 which is typically electrodes. The electrodes generally include one active electrode placed at the vertex of the subject 60, one reference electrode placed on the neck of the subject 60 and a ground electrode placed at the clavicle of the subject 60. Other configurations for the electrodes are possible. It may also be possible to use more electrodes.

The sensed EEG data is then sent to the amplifier 30 which amplifies the sensed EEG data to a level that is appropriate for the input range of the ADC 18. The amplifier 30 may use a gain of 10,000. The amplified sensed EEG data is then sent to the filter 32 which filters the amplified sensed EEG data such that sampling can be done without aliasing by the ADC 18. The filter 32 may have a lowpass setting of 300 Hz and a highpass setting of 1 Hz. The ADC 18 receives the filtered amplified EEG data and samples this data at a rate of approximately 1000 Hz. The sampling rate depends on the settings of the filter 32. Other sampling rates may also be used, however, provided that the Nyquist rate is not violated as is well understood by those skilled in the art.

The objective audiometric test apparatus 10 shown in FIG. 1a may be extended to comprise other circuitry such as attenuation circuits which may be used in the calibration of the apparatus. Other circuitry may be added to the objective audiometric test apparatus 10, to effect other audiometric tests such as performing an aided hearing test in which the subject 60 has at least one hearing aid and the objective audiometric test apparatus 10 is adapted to alter the gain of the hearing aid so that the subject 60 can hear the SSAEP stimuli which are presented to the subject 60 via free-field speakers.

The objective audiometric test apparatus 10 can clearly be embodied in various ways. For example, many different types of computers may be used. In addition, the data-acquisition board 14 may have both multiple inputs (ADCs) and multiple outputs (DACs). Multiple inputs may be used when SSAEP responses are recorded at multiple electrode sites on the subject 60 and the EEG data obtained from these electrode sites are used to increase the SNR of the SSAEP responses. Furthermore, principal component analysis, or source analysis, may be used, where the variance of the EEG data points are projected onto at least one dipole source and data not related to the dipole source are removed from the EEG data, thereby separating signal from noise. Multiple outputs may also be used (e.g. 8 DACs) to create the acoustic stimuli that are presented to each ear of the subject 60. This would allow some components of the SSAEP stimulus to be manipulated independently from the others. For example, multiple DACs may allow a band-limited noise-masker to be increased in intensity when the SSAEP response to a particular SSAEP stimulus, presented through one of the DAC channels, becomes significant.

The software program 40, also known as the MASTER (Multiple Auditory Steady-State Response) program allows a user to select a particular auditory test to perform on the subject 60. The software program 40 is preferably programmed using the LabVIEW™ software package available from National Instruments, but could be instantiated with other software packages. The software program 40 comprises a plurality of modules which are not all shown in FIG. 1a to prevent cluttering the Figure. The software program 40 controls test signal generation via the signal creator module 42 and the modulator module 44. The software program 40 also allows the operator to select from a number of objective audiometric tests which will be discussed later in more detail. The signal creator module 42 creates data series for the carrier signals that are used in the SSAEP stimulus. The signal creator module 42 will typically employ the modulator module 44 to amplitude modulate and/or frequency modulate these carrier signals. The software program 40 then controls analog to digital conversion and digital to analog conversion according to the protocol of the auditory test that is being performed.

The software program 40 then analyzes the sensed EEG data via the analysis module 46 which includes the noise reduction module 48 and the response detection module 50. As previously described, the SNR of the SSAEP response is quite small. Therefore, the sensed EEG data must be processed to reduce background noise. Accordingly, the noise reduction module 48 may employ sample weighted averaging, time averaging and/or adaptive artifact rejection (which will all be described later in more detail). The reduced noise signal is then sent to the detection module 50 to determine whether at least one SSAEP response is present within the data. The detection module 50 may employ the phase weighted t-test, the phase zone technique or the MRC method which will later be described in more detail.

The software program 40 can also display test results in the frequency domain on the display monitor 36. The software program 40 can also save the test results on the storage device 34 which may be a hard drive or the like for further extensive analysis by other programs. The software program 40 also allows the test results to be printed by a printer (not shown).

The software program 40 also communicates with the master database 52 which comprises a plurality of databases D1 to Dn. Only a few of these databases have been shown in FIG. 1 for reasons of clarity. The databases contain normative data from sample populations of subjects relating to a variety of parameters for SSAEP testing. For instance, the databases include normative phase data which can be used to create an optimal vector SSAEP stimuli having amplitude and frequency modulated components which are adjusted to evoke SSAEP responses with increased amplitudes. The databases further contain information about the amplitude of SSAEP responses to various SSARP stimuli.

The software program 40 implements a graphical user interface which consists of a series of interactive screens. These interactive screens allow a user to control the software program 40, perform a desired auditory test and analyze test results. The interactive screens comprise a Main screen, a Stimulus Set-Up screen, a View Stimulus screen, a Recording Parameters screen, a Record Data screen, a Process Data screen and several Test Result summary screens.

The Main screen permits the user to select a particular audiometric test to perform. The Main screen also allows the user to navigate through the various other screens that are available.

The Stimulus Set-Up screen permits the user to define up to 8 SSAEP test signals which can be combined in a multiple SSAEP stimulus that can be presented to both ears of the subject 60. Other embodiments of the invention will allow more than eight stimuli to be presented. For example, eight stimuli may be presented to each of the two ears of the subject 60 for a total of 16 stimuli. The user can define the frequency of the carrier signal (i.e. carrier frequency), the frequency of the modulation signal (i.e. modulation frequency), the amplitude modulation depth, the frequency modulation depth, the stimulus intensity, and the phase of the frequency modulation component relative to the phase of the amplitude modulation component for a particular type of SSAEP stimulus. The Stimulus Setup-Up screen therefore allows the user to choose the SSAEP stimulus to comprise an amplitude modulation test signal (AM), a frequency modulation test signal (FM), a combined amplitude modulation and frequency modulation test signal (referred to as mixed modulation or MM), an optimum vector combined amplitude modulation and frequency modulation test signal (OVMM) and an independent amplitude modulation and frequency modulation test signal (IAFM). Furthermore, the user can also define the envelope of the carrier signal by choosing a particular modulation signal. In particular, the user can choose a sinusoidal signal as the modulation signal or an exponential modulation signal as the modulation signal. Some exemplary exponential modulation signals include a sinusoid that has an exponent of 2, 3, 4 or 5. Alternatively, fractional exponents may be used.

Once, the carrier frequency and modulation frequency are chosen, the signal creator 42 automatically adjusts these frequencies to ensure that an integer number of cycles of the carrier signal and modulation signal can fit in the output buffer of the DAC 16 and the input buffer of the ADC 18 This is important to avoid spectral spreading in the generated acoustic stimulus as well as to avoid spectral spreading in the sensed EEG data which are digitized by the ADC 18. The signal creator 42 may also be used to present test signals to the subject 60 with constant peak-to-peak amplitudes or constant RMS amplitudes, whereby the amplitude of the envelope of the test signal is increased to compensate for the modulation depth.

The signal creator 42 can also generate stimuli consisting of tones, broad-band noise, high-pass noise, low-pass noise, or band-pass noise all of which can be either modulated or unmodulated. In the case of noise, the signal creator 42 may allow the user to adjust the band-pass and band-stop characteristics of the noise including the roll-off of the transition region that is between the band-pass and band-stop regions. Currently the objective audiometric test apparatus 10 uses a circular buffer in the DAC 16. However, in the case of noise stimuli, the incorporation of a double buffering technique may be used where data is read from one half of the buffer and written to the other half of the buffer. The data that was just written to the buffer is then shifted to the half of the buffer where data is read from.

The Recording Parameters screen enables the user to define the rate of the ADC 18, the rate of the DAC 16 (which must be a multiple of the A/D rate) and the epoch duration (i.e. the size of the input buffer contained in the ADC 18). The user may also define an artifact rejection level, calibration coefficients, phase adjustment coefficients and whether on-line computations are made upon weighted or un-weighted (i.e. raw) data. The user may also choose amplification values for data acquisition boards which provide amplification such as the AT-MIO-16e-10 board. The artifact rejection level may be based on an absolute threshold value or upon the average amplitude of the high frequency range of the sensed EEG data.

The View Stimulus screen enables the user to view the SSAEP stimuli that will be presented to the subject 60. The View Stimulus screen also allows the user to view the amplitude spectra of the SSAEP stimuli.

The Record Data screen allows the user to view the sensed EEG data for the current epoch that is being sampled. The user can also view the amplitude spectra of the average sweep (a sweep is a concatenation of epochs and the average sweep is the result from averaging a plurality of sweeps). When the average sweep is displayed, the frequencies of the SSAEP responses in the EEG data are highlighted for easy comparison with background EEG activity (i.e. background noise). The Record Data screen also allows the user to control the acquisition of the EEG data. In addition, the Record Data screen allows the user to view both the numerical and graphical results of statistical analyses that are conducted on the EEG data to detect the presence of at least one SSAEP response to the SSAEP stimulus.

The Process Data screen enables the user to choose different methods of viewing, storing, combining and analyzing data sets, which either contain sweeps or SSAEP responses from a single subject or from a plurality of subjects. The data sets may be combined so that each sweep that goes into a final average is weighted by the amount of data from which it is created or by the number of separate data sets combined. The data sets may also be subtracted, in order to enable the user to calculate, for example, derived-band responses.

The software program 40 has options for collecting and displaying data. For example, as is commonly incorporated into clinical audiometric devices, the parameters for several clinical protocols can be stored in several parameter files to enable several tests to be run automatically, for example, each with different stimulus intensities or different SSAEP stimuli. The results for tests incorporating different SSAEP stimuli and different stimulus intensity levels can be displayed in several Test Summary screens where all of the audiometric test results of the subject 60 are presented, for example, in traditional audiogram format.

In another embodiment of the objective audiometric test apparatus 10, the hearing tests may be performed partly automatically or fully automatically and may be used to adjust a hearing aid. In the case of a hearing aid, the gain of the hearing aid may be adjusted by the objective audiometric test apparatus 10 according to the outcome of aided hearing tests that are conducted. For example, during the calibration of the hearing aid, the gain of the hearing aid for a specific frequency region may be automatically increased if an SSAEP response to a given SSAEP stimulus in that specific frequency region was not detected. In this embodiment, the objective audiometric test apparatus 10 can communicate with the hearing aid device using a physical connection, such as a ribbon cable, or via RF telemetry as is used to adjust other biomedical devices (such as implanted stimulators).

Figure 1B:
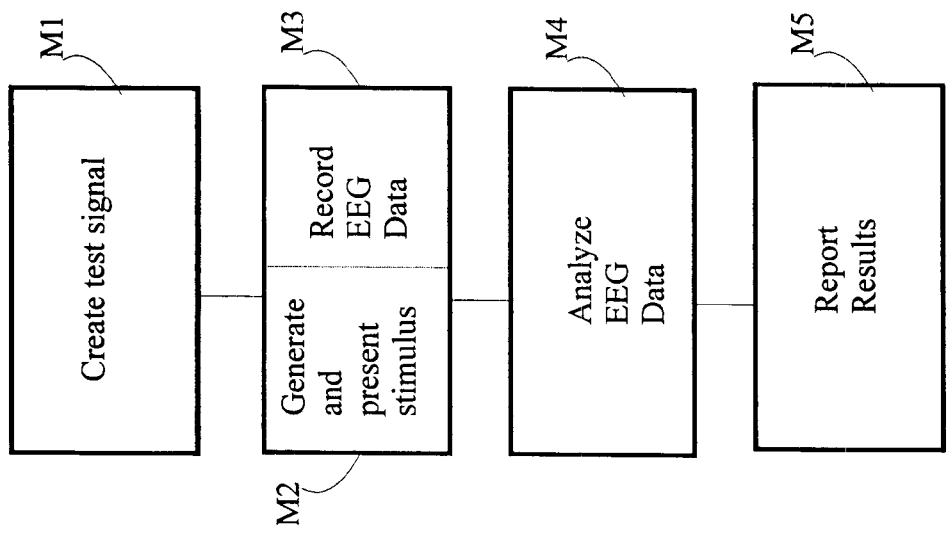
FIG. 1b is a flow diagram illustrating the general objective auditory test methodology.

FIG. 1*b* illustrates the general steps undertaken by the objective audiometric test apparatus 10. The objective audiometric test apparatus 10 first generates a test signal in step M1 which is appropriate in testing an aspect of the auditory system of the subject 60. The test signal comprises a wide variety of signals including tones, noise, amplitude modulated signals, frequency modulated signals, optimum vector amplitude and frequency modulated signals, independent amplitude and frequency modulated signals, signals which have envelopes that are modulated by an exponential modulation signal, and the like. Accordingly, this step may comprise selecting a test signal and then modulating the test signal to obtain a modulated test signal. This procedure may also be done on more than one test signal so that the test signal comprises at least one modulated test signal. The next step M2 is to transduce the test signal to create a stimulus and present this stimulus to the subject 60. The next step M3 is to record the EEG data of the subject 60 simultaneously with presentation of the stimulus. The presentation of the stimulus and the acquisition of the EEG data must be synchronized with the objective audiometric test apparatus 10 to accurately represent signals of interest. The next step M4 consists of analyzing the recorded EEG data to determine whether there are any responses present in the EEG data. This step will typically involve performing a noise reduction method on the EEG data and then applying a detection method to the noise reduced data. The next step M5 may be to report test results. The steps outlined in FIG. 1*b* may be part of a larger audiometric test that will involve performing each of the steps several times. These particular audiometric tests and the steps which are involved are discussed in more detail below.

SSAEP Detection

The EEG data that is sensed during the presentation of a multiple SSAEP stimulus contain superimposed responses to the multiple components of the SSAEP stimulus as well as background noise. Accordingly, it is difficult to distinguish the SSAEP responses in the time domain. However, if the EEG data is converted into the frequency domain, using a Fast Fourier Transform (FFT) for example, the amplitude and phase of each SSAEP response can be measured at the specific frequency of each modulation signal in the multiple SSAEP stimulus.

As previously stated, the SNR of the SSAEP response is very small. Accordingly, a large amount of EEG data needs to be collected to increase the SNR of the SSAEP data. Conventional approaches to increase the SNR of the SSAEP response include artifact rejection and time averaging. These conventional approaches are implemented by the analysis module 46 since these techniques are still fairly popular with clinicians and research scientists in the field of audiometry.

As previously mentioned, epochs of EEG data are acquired during SSAEP testing. Artifacts may contaminate the data and introduce large noise spikes that are due to non-cerebral potentials such as movement of facial muscles or the like. Accordingly, artifact rejection involves analyzing each epoch to determine if the epoch contains data points that are higher than a threshold level such as 80 $\mu V$. Artifact rejection is useful in removing spurious noise components to noise reduction techniques such as time averaging to be more effective. The noise reduction module 48 is adapted to effect artifact rejection on the epochs which are recorded. If an epoch is rejected, the next epoch that does not exceed the artifact rejection threshold is concatenated to the last acceptable epoch. This concatenation procedure does not cause discontinuities in the data because the SSAEP stimulus which evokes the SSAEP response is constructed so that each epoch contains an integer number of periods of the SSAEP response.

Time averaging comprises concatenating epochs to form sweeps. A plurality of sweeps are then averaged in time to yield an average sweep. Time averaging reduces the level of background noise activity that are not time-locked to the stimuli. After the average sweep is obtained, it is converted into the frequency domain via the FFT. In this case, the sweep duration is an issue since increasing the sweep duration distributes the background noise power across more FFT bins without affecting the amplitude of the SSAEP response which is confined to a single FFT bin since the SSAEP response occurs at a single frequency and the noise is broadband. Thus increasing the duration of the sweep increases the frequency-resolution of the FFT. The specific frequencies available from the FFT are integer multiples of the resolution of the FFT which is 1/(Nt), where N is the number of data points and t is the sampling rate. One possible implementation uses a sampling rate of 1000 Hz, an epoch length of 1024 points and sweeps that are 16 epochs long (16,384 points). Accordingly, the resulting frequency resolution is 0.61 Hz (1/(16*1.024*0.001)) and the frequency region in the FFT spans DC (0 Hz) to 500 Hz. Alternatively, sweeps may also be 8 epochs long or 12 epochs long.

The detection module 50 may provide a noise estimate which is derived from neighboring frequencies in the amplitude spectrum (i.e. FFT) at which no SSAEP response occurs. If there were no SSAEP response in the recorded data then the power at the modulation frequency, where the response should occur, would be within the range of the noise power at the neighboring frequencies. An F-ratio may then be used to estimate the probability that the amplitude at the modulation frequency in the resulting FFT is not statistically different from the noise estimate. When this probability is less than 0.05 (p<0.05), the SSAEP response may be considered significantly different from noise, and the subject 60 is considered to have heard the SSAEP stimulus. A more stringent criteria of p<0.01 can also be chosen. Currently, the objective audiometric test apparatus 10 provides an F-Ratio where each SSAEP response in the amplitude spectrum associated with a frequency of modulation is compared to the FFT data in 60 noise bins above and 60 noise bins below the FFT bin that contains the SSAEP response. Accordingly, this ratio is evaluated as an F-statistic with 2 and 240 degrees of freedom.

The objective audiometric test apparatus 10 further comprises the noise reduction module 48 which may be adapted to employ artifact rejection in which epochs are rejected based on high frequency activity. Artifact rejection which simply chooses a threshold based on the sensed potentials may not be optimally efficient because low-frequency high-amplitude EEG activity (e.g. less than 20 Hz) dominates the amplitude of the sensed EEG data. Thus the noise in the vicinity of the SSAEP response, which may be in the frequency range of 70 to 200 Hz, is not appropriately represented by the recorded EEG data. Accordingly, rejecting epochs based upon the mean amplitude of the high frequency EEG noise may be more appropriate.

In addition, the noise reduction module 48 may employ an adaptive artifact rejection method in which an adaptive threshold value is calculated which depends on a statistical property of the data points in an epoch. This method comprises calculating the standard deviation of the data points in the epoch and setting the threshold value to be two times the calculated standard deviation value. If the epoch contains data which is over this threshold limit, then the epoch is rejected. This rejection method may be performed offline, after the sensed EEG data has been recorded from the subject 60 or the method may be performed online while the sensed EEG data is being recorded from the subject 60. The online artifact rejection method may provide an idea of how much EEG data needs to be recorded from the subject 60 based on the number of epochs which are rejected. Alternatively, this adaptive artifact rejection method can be done after the epoch is filtered by a bandpass filter having a passband which is substantially similar to the frequency region in which the SSAEP response may occur (i.e. 70 to 110 Hz or the frequency range of 120 to 250 Hz). Alternatively, other statistical measures may be used to adaptively set the artifact rejection threshold.

The noise reduction module 48 may further employ sample weighted averaging to reduce the noise in the sensed EEG data. Under the sample weighted averaging method, epochs are concatenated into sweeps of sufficient duration. A plurality of sweeps are formed and aligned such that a matrix is formed where the sweeps are the rows of the matrix and the epochs are the columns of the matrix. Each sweep is filtered and the epochs along each column are then weighted by an estimate of the noise variance that is local to the frequency region in which the SSAEP response resides. The noise variance estimate is local to the frequency region in which the SSAEP response resides because the bandpass filtering of the sweeps is done such that the passband of the filter is substantially similar to the frequency region in which the SSAEP response should occur. For example, the passband of the bandpass filter may be from 70 to 110 Hz. The epochs are then weighted by the inverse of this noise variance after the noise variance has been normalized. The weighted epochs along each column of the matrix is then summed to yield a resulting sweep which has a reduced noise component compared to the case of simply performing time averaging on the plurality of sweeps. Alternatively, noise weighted averaging may be used where the amplitudes of the steady-state responses are removed from the noise estimate.

In pseudo-code format, sample weighted averaging is effected according to the steps of:

a) obtaining a plurality of epochs while sensing EEG data from the subject 60 while simultaneously presenting the SSAEP stimulus;

b) forming a plurality of sweeps by concatenating the epochs together;

c) filtering each sweep to obtain a plurality of filtered sweeps;

d) aligning each sweep to form a first matrix in which the sweeps are the rows of the matrix and the epochs within the plurality of sweeps are the columns of the matrix and aligning each filtered sweep in a similar fashion to form a filtered matrix which is used to calculate weights;

e) calculating the variance of each epoch in the filtered matrix to obtain a noise variance estimate for each epoch in the filtered matrix;

f) normalizing the noise variance estimate for each epoch in the filtered matrix by dividing the noise variance estimate for each epoch in the filtered matrix by the sum of all noise variance estimates for the epochs along the column of the filtered matrix which contains the epoch to obtain a normalized noise variance estimate for each epoch;

g) inverting each normalized noise variance estimate to obtain a weight for each epoch and multiplying each corresponding epoch in the first matrix by its respective weight to obtain a plurality of weighted epochs; and, h) summing all of the weighted epochs in the first matrix along the columns of the first matrix to obtain a signal estimate.

Referring to FIGS. 2a–2h, sample weighted averaging and artifact rejection (based on the mean amplitudes of higher frequency regions) are compared to normal averaging. The results show that sample weighted averaging results in SSAEP responses with the higher SNR. FIG. 2a shows a histogram for amplitudes of recorded EEG data points for a noisy recording (i.e. there were many artifacts during the recording, the amplitudes of which are identified by arrows in FIG. 2a). FIG. 2b also shows a histogram for amplitudes of the recorded EEG data for a quiet recording (i.e. there were not many artifacts during the recording). The data points in FIGS. 2a and 2b were obtained from the same subject who was presented a multiple SSAEP stimulus comprising eight test signals at 50 dB SPL. FIGS. 2c and 2d show the results from analyzing the data using normal averaging. The SSAEP responses that have been detected are denoted by the filled arrowheads. In FIG. 2c, only four of the eight SSAEP responses have been detected meanwhile in FIG. 2d, all eight of the SSAEP responses have been detected. FIGS. 2e and 2f show the results from analyzing the EEG data using sample weighted averaging. In FIG. 2e, seven SSAEP responses have been detected and in FIG. 2f, eight SSAEP responses have been detected. Furthermore, comparing FIG. 2e with FIG. 2c shows that sample weighted averaging has detected 3 more SSAEP responses as well as increased the average SNR of the SSAEP responses by a factor of over 2. FIGS. 2g and 2h show the results from analyzing the EEG data using amplitude rejection in which rejection was based on the mean amplitude of the EEG data in the higher frequency region. FIG. 2g shows that this form of artifact rejection resulted in seven SSAEP responses being detected while FIG. 2h shows that all eight SSAEP responses were detected.

Referring now to the detection module 50, a phase weighted t-test is used to detect the presence of SSAEP responses in the recorded EEG data. The phase weighted t-test employs data biasing to detect the SSAEP response based on a priori knowledge about the SSAEP response. In particular, if the phase of the SSAEP response is known, then the EEG data can be biased so that statistical analysis (i.e. the detection method) is more likely to recognize an SSAEP response with a phase that is similar to the expected phase than noise data with a completely different phase. The biasing of the data points is done by employing a weighting function that provides larger weights for SSAEP responses that have a phase which is close to the expected phase value. The phase weighted t-test allows phase-weighting without the need for empirical compensation of the probability level at which the SSAEP response is detected.

Since the recorded EEG data is processed by the FFT, the resulting data points are two-dimensional and have real and imaginary components. The FFT bins which represent the SSAEP response and the surrounding noise can be projected onto a single dimension oriented at the expected phase by using the equation:

$$p_i = a_i * \cos(\theta_i - \theta_e) \quad (1)$$

where
- $p_i$ is the projected value;
- $a_i$ is the amplitude of an FFT component (i.e bin);
- $\theta_i$ is the phase of the FFT component; and,
- $\theta_e$ is the expected phase of the response.

An upper confidence limit, based on the amplitude of the projected FFT components that contain noise can then be estimated using a one-tailed Student t-test with $p<0.05$ (to reduce the number of false positives, $p<0.01$ can be used). An SSAEP response can then be recognized as being statistically significantly greater than noise (i.e. detected) if the projected value of the FFT component whose frequency is the same as that of the SSAEP responses which is being detected is larger than the upper confidence limit.

The steps to employ the phase weighted t-test on the EEG data points include the following steps:

a) forming a plurality of sweeps from the EEG data points;

b) averaging the plurality of sweeps to obtain a plurality of averaged data points;

c) calculating a plurality of Fourier components for the plurality of averaged data points wherein the Fourier components are calculated for the frequency region where the response should occur and adjacent frequencies thereof (for noise estimation);

d) calculating the amplitude ($a_i$) and phase ($\theta_i$) for the plurality of Fourier components which were calculated in step (c);

e) biasing the amplitudes ($a_i$) to obtain biased data points ($p_i$) according to the formula:

$$p_i = a_i * \cos(\theta_i - \theta_e)$$

where $\theta_e$ is the expected phase value (this is done for the Fourier component at which the response should occur as well as for adjacent Fourier components which represent noise);

f) calculating upper confidence limits using a one tailed Student t-test on the biased amplitudes which represent noise in the vicinity of Fourier components where the response should occur; and g) comparing biased amplitudes of Fourier components where the response should occur to the upper confidence limits to determine if the biased amplitudes are larger than the upper confidence limit.

If the biased amplitudes for the response is larger than the upper confidence limit, then the response is detected; otherwise no response is detected. Note that in the above method, some preprocessing techniques can be used on the plurality of data points to reduce the background EEG noise amplitude in the plurality of data points by the noise reduction module 48. These preprocessing techniques may include artifact rejection, adaptive artifact rejection, time averaging and sample weighted averaging.

Figure 3A:
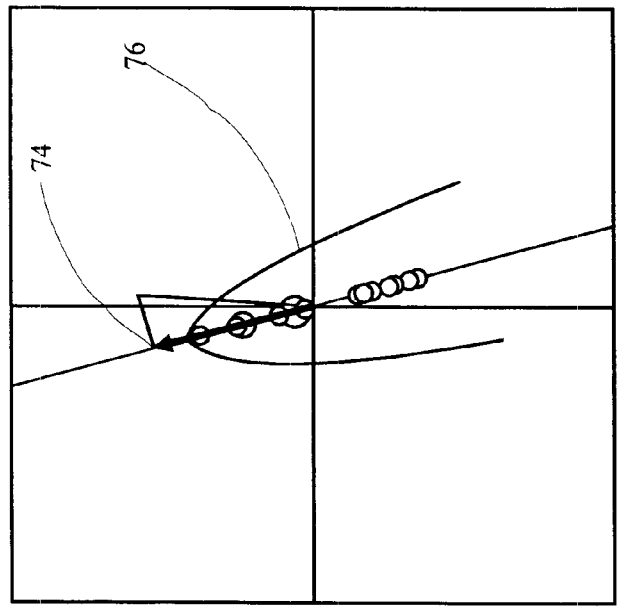
FIG. 3a is a plot of the results of the F-test on an averaged sweep of EEG data points containing an SSAEP response.
Figure 3B:
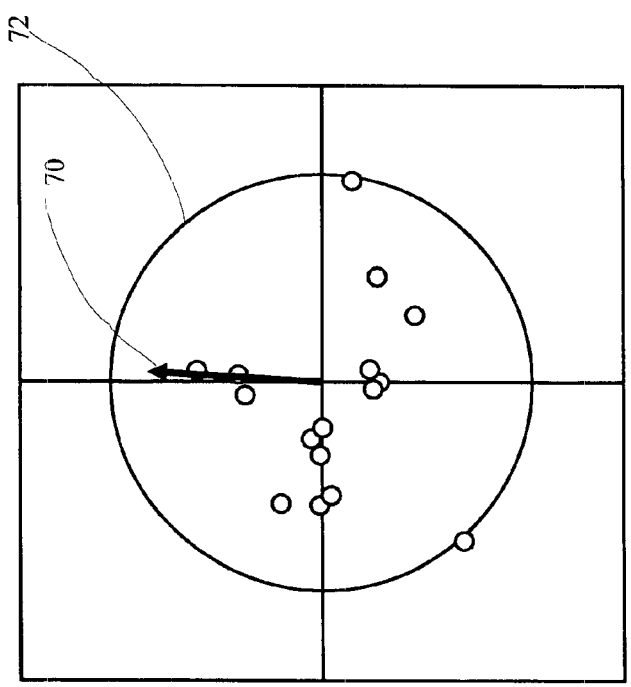

Referring to FIGS. 3a and 3b, the use of a phase weighted t-test is illustrated on some sample data. FIG. 3a shows that the response 70 is within the upper confidence limits which are defined by the circle 72. The upper confidence limits 72 were obtained according to the procedure previously described using two-dimensional F-statistics. The SSAEP response 70 is therefore not statistically significant (i.e. not detected) since the magnitude of the SSAEP response 70 is not larger than the upper confidence limit 72. However, knowing that the expected phase of the SSAEP response should be 104 degrees, in this example, allows for the use of the phase weighted t-test which is shown in FIG. 3b. Biasing the FFT components that represent noise results (i.e. the open circles in FIG. 3b) results in upper confidence limits 76 that are now shown by a parabola (the actual upper confidence limit is the single point where the parabola intersects the line of the expected phase). Notice that the apex of the parabola 76 has a smaller excursion from the origin as compared to the circle 72 which makes it easier to detect an SSAEP response if its phase is similar to that which is expected. The SSAEP response is now biased by projecting it on the expected phase of 104 degrees. The SSAEP response 74 now extends beyond the confidence limits 76 of the projected noise measurements. The SSAEP response is considered to be statistically significant and therefore detected with the same number of noise data points shown in FIG. 3a.

In the case of the multiple SSAEP stimulus which contains multiple signals that evoke multiple SSAEP responses, the phase weighted t-test is repeated for each of the expected SSAEP responses, with each response having a different expected phase since they were evoked by test signals having various carrier frequencies.

The formula in equation (1) for biasing the amplitudes based on the difference between the measured phase and the expected phase can be made broader or tighter depending on the weighting function that is used. For instance, the cosine weighting in equation 1 can be replaced with a cosine squared function in order to more strongly punish values that deviate from the expected phase. Alternatively, the 'tightness' of the weight function can be adjusted according to the normative inter-subject or intra-subject variance of expected phase values. For example, the standard deviation for the measured phase values in a normative database, contained within the master database 52 can be normalized and used to weight the difference between the expected and observed phases in equation 1.

Furthermore, phase coherence measurements can be biased toward an expected phase in exactly the same way as was done for the phase weighted t-test, whereby the phase coherence estimate is biased by the difference between the expected and observed phases. Additionally, these methods of biasing the data can be used to evaluate responses in average sweeps, single sweeps, or even across individual epochs.

Alternatively, the average sweep is not always calculated and the presence of a response can be statistically assessed by assessing the SSAEP responses for each sweep or even for each epoch.

Several approaches can be used to define the expected phase. First and foremost, a database of normative expected phase values are collected and stored in the master database 52. These normative expected phase values can be obtained by collecting the average phases of SSAEP responses obtained from a group of normal subjects (who may be matched for age and gender) who were presented with similar stimuli. Another approach is to estimate the expected phase from previously recorded data on the particular subject who is currently being tested. For example, if an SSAEP response at 60 dB SPL has a phase of 80 degrees then one may use this value or a slightly smaller phase as the expected phase for the SSAEP response that is recorded during a test with a similar SSAEP stimulus that is at 50 dB SPL. Alternatively, the phase measured from several earlier sweeps of a recording period may be used to obtain an estimate of the phase for the sweeps which are taken later in the recording period. Another alternative would be in the case of the multiple SSAEP stimulus which contains individual SSAEP stimuli at different carrier frequencies. In this case, the phases of the SSAEP responses that have reached statistical significance (i.e. been detected) during a given testing period can be used to estimate what the phase should be for SSAEP responses that have not yet reached significance. For example, if the phase of a response to an SSAEP stimulus with a carrier signal comprising a 1000 Hz tone that is amplitude modulated at 80 Hz is 45 degrees and the phase of a response to an SSAEP stimulus with a carrier signal comprising a 4000 Hz tone that is amplitude modulated at 90 Hz is 90 degrees then the predicted phase for an SSAEP response to an SSAEP stimulus that with a carrier signal comprising a 2000 Hz tone that is amplitude modulated at 85 Hz that has not reached significance may be interpolated as being 60 degrees. Other interpolation methods may be used.

The detection module 50 may be further adapted to perform a phase zone method to detect the presence of SSAEP responses in recorded EEG data. While the statistical detection methods of the prior art, rely on the probability of phases randomly occurring, a statistical detection method may be made stronger if the distribution of phases is expected to lie within a given number of degrees (i.e. the target phase range) from an expected phase value. For example, if the expected phase of a given response is 90 degrees, then the chance of the phase value landing within N degrees of the expected phase is (N/360). Accordingly, if N is set at 90 and the expected phase is 70 degrees, then there is a 1 in 4 chance that each calculated phase value of a recording without an SSAEP response will occur between 25 and 115 degrees (i.e. the target phase range). The number of phases that fall within the target phase range can be compared to the number of phases which fall outside of the target phase range using binomial analysis, with a probability of 0.25 (i.e., 1 in 4) for this example. However, if the variance of the calculated phases is small, then the target phase range may also be made smaller (i.e. a target phase range less than 90 degrees). This will allow the SSAEP response to become statistically significant (i.e. detected) with a smaller amount of EEG data points since the binomial probability index will get smaller as the target phase range gets smaller In terms of SSAEPs, the phase zone method is effected by analyzing each sweep of data rather than using the average sweep as is done in the F-test. The method consists of the steps of:

a) presenting the SSAEP stimulus to the subject 60;
    b) sensing the EEG from the subject 60 while substantially simultaneously presenting the stimulus to the subject 60 to obtain a plurality of data points;
    c) separating the plurality of data points into sweeps;
    d) calculating a Fourier component for the frequency at which the response should occur for each sweep;
    e) calculating a phase value for each Fourier component;
    f) calculating a phase target range;
    g) calculating the number of phases (Na) from step (e) that are within the target phase range; and,
    h) using binomial analysis to analyze Na to determine whether said plurality of data points contains a response.

The phase target range can be calculated based on a database of normative expected phases, stored within the master database 52, that are correlated to the subject and the SSAEP stimulus characteristics.

The detection module 50 may be further adapted to perform another statistical method for detection referred to as the MRC method. The use of an expected phase angle has been incorporated as a variant of the Rayleigh test for circular uniformity (RC) termed the modified Rayleigh test (MRC). The RC method can be made more statistically powerful if an expected phase angle is known. Hence the MRC is developed which weights the RC value with a weighting function that incorporates the expected phase according to the following equation:

$$MRC = RC * \cos(\theta_a - \theta_e) \qquad (2)$$

where $\theta_a$ is the vector-averaged angle of the data set and $\theta_e$ is the expected angle.

In addition to detecting responses at the modulation frequencies used in the SSAEP stimulus, the detection module 50 may be adapted to detect the SSAEP responses that occur at the carrier frequency. In this case, the sampling rate of the ADC 18 would have to be increased so that EEG data with frequency content in the range of the carrier frequency could be properly sampled. However, this EEG data may be difficult to interpret because stimulus artifacts, which are created by electromagnetic inductance, will add to the sensed EEG data and distort the data. These artifacts can be minimized by various techniques such as shielding the transducer 26 and separating it from the recording instrumentation (i.e. the sensors 28, the amplifier 30 and the filter 32). In addition, the use of insert earphones with a greatly extended air-tube can aid in overcoming stimulus artifacts (provided that the transfer function of the transducer is adapted to compensate for the filtering effect of the lengthened tube). Another technique to remove the stimulus artifact may be based on the fact that the stimulus artifact changes its amplitude linearly with changes in the intensity of the SSAEP stimulus while the latency of the stimulus artifact does not change, whereas an SSAEP response will show non-linearities in its intensity relationship and will change latency. Thus, if EEG data is recorded at more than one stimulus intensity, algorithms may be constructed to remove the stimulus artifacts based on its linearity with respect to stimulus intensity.

SSAEP Stimuli

The objective audiometric test apparatus 10, via signal creator 42 is adapted to construct a variety of test signals which can be used in the SSAEP stimulus. These test signals include tones, amplitude modulated signals (AM), frequency modulated signals (FM), an optimum vector combined amplitude modulated and frequency modulated signals (optimum vector mixed modulation or OVMM) and independent amplitude modulated and frequency modulated signals (IAFM). The modulator 44 may also be used with the signal creator 42 to provide envelope modulation with an exponential modulation signal. The signal creator 42 can also generate test signals consisting of broad-band noise, high-pass noise, low-pass noise, or band-pass noise all of which can be either modulated or unmodulated.

The signal creator 42 generates the optimum vector combined amplitude modulation and frequency modulation (OVMM) test signal such that the amplitude modulation rate is the same as the frequency modulation rate. Furthermore, the phase of the frequency-modulated component of the OVMM test signal is adjusted with respect to the phase of the amplitude modulated component of the OVMM test signal such that the SSAEP response evoked from the subject has an increased amplitude.

Referring to FIGS. 4a–4f, the amplitudes of SSAEP responses to an SSAEP stimulus consisting of an AM test signal (open square data points) and an SSAEP stimulus consisting of an MM test signal (filled in circular data points). The data was collected from eight test subjects. The SSAEP responses were obtained for a variety of carrier frequencies, stimulus intensities and frequency modulation depths. FIGS. 4a–4f show that the MM SSAEP stimulus evoked SSAEP responses with larger amplitudes than the AM SSAEP stimulus for a variety of stimulus intensities and carrier frequencies. The frequency modulation depth for the MM SSAEP stimulus was 25% for FIGS. 4a–4c and 10% for FIGS. 4d–4f (the frequency modulation depth indicates the frequency deviation from the carrier frequency in the SSAEP stimulus). The amplitude modulation depth was 100% for the AM SSAEP test results shown all Figures. In FIGS. 4a–4c, at 50, 40 and 30 dB SPL, the amplitudes of the SSAEP response were 30%, 49%, and 28% larger for responses evoked by the MM SSAEP stimulus as compared to those evoked by the AM SSAEP stimulus. FIGS. 4d–4f show results from a different group of eight subjects in which the SSAEP response amplitudes were 20%, 7%, and 8% larger when using MM SSAEP stimuli. These Figures also show that it is possible to obtain enhanced response amplitudes near threshold using frequency modulation depths near 25%.

For the test results shown in FIGS. 4a–4h, the MM SSAEP stimuli were not adjusted to evoke SSAEP responses with optimal amplitudes. When an optimum vector mixed modulation signal is used, the SSAEP response amplitudes are larger for the higher frequency test results (i.e. 4000 to 6000 Hz). It should also be noted that the use of an FM depth of 10% in the MM SSAEP stimulus is not sufficient to increase the SSAEP response amplitudes as compared to the response amplitudes obtained when using the AM SSAEP stimulus. Rather, an FM depth of 25% is needed to evoke larger amplitude SSAEP responses as is shown in FIGS. 4b and 4c.

Figure 5B:
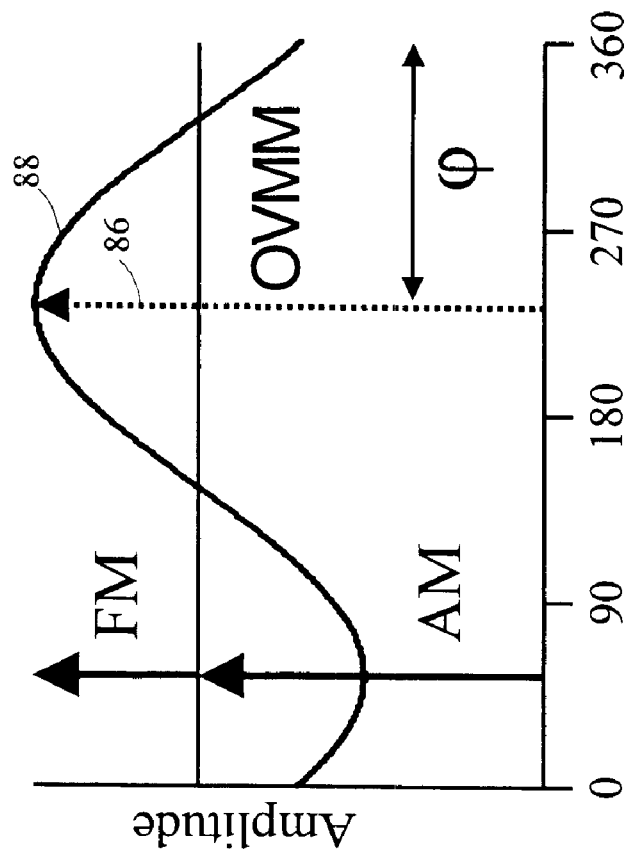
FIG. 5b is a graph illustrating how the response to an SSAEP stimulus containing amplitude modulated and frequency modulated components can be modeled as a sinusoid when the phase of the frequency modulated component of the SSAEP stimulus is varied with respect to the phase of the amplitude modulated component of the SSAEP stimulus.
Figure 5A:
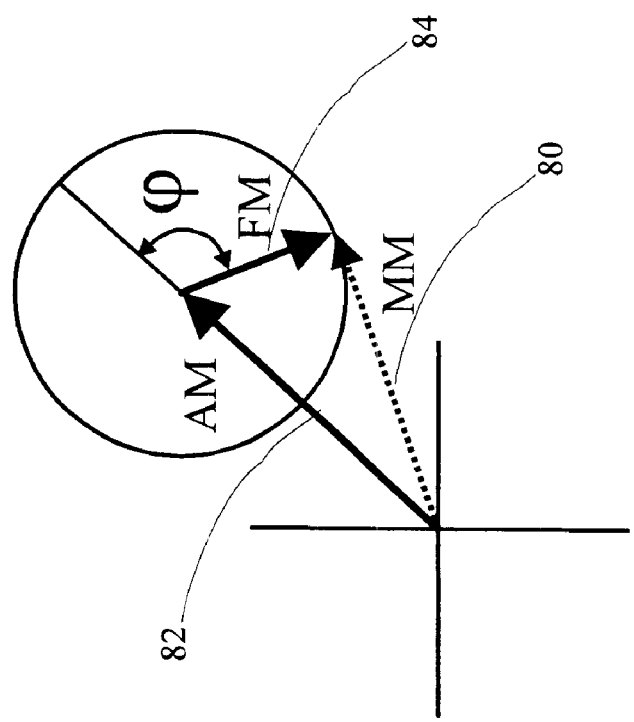
FIG. 5a is a plot illustrating how the response to an SSAEP stimulus containing amplitude modulated and frequency modulated components can be modeled as the vector addition of the SSAEP response to the amplitude modulated component of the SSAEP stimulus and the SSAEP response to the frequency modulated component of the SSAEP stimulus.

Referring to FIG. 5a, adjusting the phase of the FM component of the MM SSAEP stimulus relative to the phase of the AM component results in SSAEP responses with different amplitudes. At one particular phase the response will be larger than at other phases. This is the basis of the optimum-vector mixed modulation stimulus. This adjustment is based on the principle that the SSAEP response 80 to an MM SSAEP stimulus is the vector sum of the response to the AM component 82 of the SSAEP stimulus and the FM component 84 of the SSAEP stimulus, in which the components are independent or only interact to a small degree. The SSAEP response to the AM component 82 is shown as the vector originating at the origin. Added to the SSAEP response to the AM component 82 is the response to the FM component 84 of the SSAEP stimulus which has a different phase than the SSAEP response to the AM component 82. These SSAEP responses were evoked by an SSAEP stimulus in which the FM component had the same phase as the AM component so that the relative phase between the AM and the FM components of the SSAEP stimulus was zero. As is evident from FIG. 5a, this results in an SSAEP response to the MM stimulus that is smaller than the response to the AM stimulus alone.

Referring to FIG. 5b, if the phase of the FM component of the SSAEP stimulus was adjusted relative to the phase of the AM component of the SSAEP stimulus in a range from 0 to 360 degrees there would be a variation in the amplitude of the response 86 which could be modeled as a sinusoid. Increases in the phase of the FM component of the SSAEP stimulus will rotate the FM response vector 84 clockwise. The SSAEP response to the MM SSAEP stimulus for any phase value of the FM component relative to the AM component of the SSAEP stimulus can then be obtained by drawing a vector straight up from the x-axis to the response curve 88. This line would be drawn at the point on the x-axis which is the value of the phase of the FM component with respect to the AM component for the SSAEP stimulus. One example of a possible response is shown as the dotted-line vector 86 which also happens to be the largest response amplitude. In this case, the SSAEP response 84 to the FM component of the SSAEP stimulus and the response 82 to the AM component of the SSAEP stimulus will line up to produce an optimum vector mixed-modulation (OVMM) stimulus, which should produce the largest MM response when the relative phase between the phase of the FM component and the AM components of the SSAEP stimulus is $\phi$. FIG. 5b thus indicates how the angle (p can be derived using several MM response amplitudes obtained as the relative phase between the FM and AM components of the SSAEP stimulus is varied. The resulting SSAEP response amplitudes can be fit with a sine wave having a baseline-offset (as shown in FIG. 5b). The size of the baseline-offset is equivalent to the amplitude of response to the AM component of the SSAEP stimulus and the amplitude of the sine wave is equivalent to the amplitude of the response to the FM component of the SSAEP stimulus.

These stimuli are called optimum-vector mixed modulation (OVMM) stimuli to distinguish then from other MM stimuli where the relative phases of the AM and FM components are arbitrarily set. OVMM SSAEP stimuli can therefore be used to evoke SSAEP responses with larger amplitudes. This is beneficial since SSAEP responses with larger amplitudes have larger SNR which should allow for SSAEP response detection in a smaller amount of time.

The process to test with OVMM SSAEP stimulus follows the following steps:
  a) create a test signal which contains at least one combined amplitude modulation and frequency modulation signal in which the phase of the FM component of the test signal is adjusted relative to the phase of the AM component of the test signal such that an increased response can be evoked from a subject;
  b) creating the test signal further comprises choosing the carrier frequency of the AM component to be substantially similar to the carrier frequency of the FM component and the modulation frequency of the AM component to be substantially similar to the modulation frequency of the FM component;
  c) transducing the test signal to create an acoustic stimulus and presenting the acoustic stimulus to the subject;
  d) sensing potentials from the subject while substantially simultaneously presenting the acoustic stimulus to the subject; and,
  e) analyzing the sensed potentials to determine whether they contain data indicative of at least one steady-state response to the acoustic stimulus.

Testing with OVMM SSAEP stimuli preferably utilizes a database of normative optimal phase values, stored within the master database 52, that may be used to adjust the phase of the FM component of the OVMM SSAEP stimulus relative to the AM component of the OVMM SSAEP stimulus. This basically entails creating a database of normative values. The database is stored in the master database 52. The database of normative values can contain phase difference data (i.e. difference between the phases of the FM and AM components of the OVMM SSAEP stimulus) which is correlated to subject characteristics and stimulus characteristics. Subject characteristics typically include the age of the subject, the sex of the subject and the like. Stimulus characteristics include the carrier frequency of the FM or AM component, the intensity of the stimulus, the AM modulation depth, the FM modulation depth and the like.

The following steps may be followed to create the database of normative phase difference data:
  a) Select a sample population to test which is correlated to a group of subjects who will be examined; i.e., if testing will be performed on newborn infants then a sample of 100 subjects may be tested, who may be appropriately matched for age and for sex;
  b) Record EEG data from the sample population that contain responses to SSAEP stimuli which contain AM components only and responses to SSAEP stimuli which contain FM components only; this testing should be done for each of the stimuli which will be used when examining the group of subjects from step (a);
  c) Detect the SSAEP responses in the recorded EEG data and measure the phase of each SSAEP response;
  d) Calculate the differences in the phases measured in step (c) between the SSAEP responses to the AM component only SSAEP stimuli and the FM component only SSAEP stimuli and plot the resulting SSAEP response amplitudes (which is the vector summation of the responses to the AM component only SSAEP stimuli and the FM component only SSAEP stimuli) to obtain a waveform as shown in FIG. 5b; and,
  e) Find the phase difference for which the resulting vector summation of the response amplitudes for the AM and FM components result in a maximum amplitude; this phase value is then used in the OVMM SSAEP stimulus to evoke increased responses from test subjects.

The signal creator 42 can also generate another test signal comprising an AM component and an FM component wherein these two components are independent from each other in that they evoke SSAEP responses that are independent from each other. This property holds true for a multiple SSAEP stimulus that contains multiple independent AM and FM components. Accordingly, the test signal is referred to as an independent amplitude and frequency modulation signal (IAFM). The IAFM signal has an AM modulation frequency that is different from the FM modulation frequency.

Figures 6A, 6B:
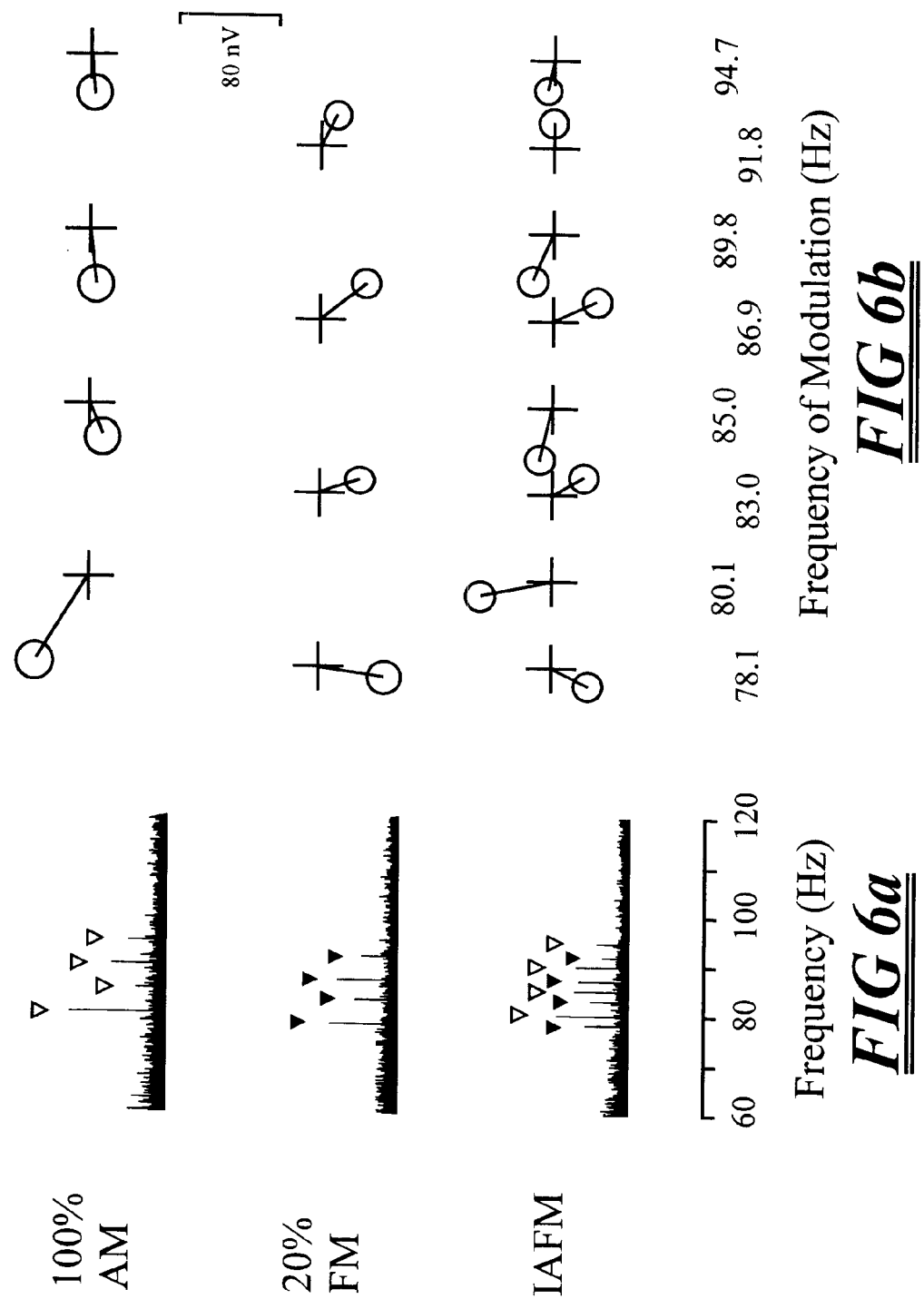

Referring to FIG. 6a, a partial view of the amplitude spectrum of the SSAEP responses for a multiple SSAEP stimulus that contains AM test signals having 100% amplitude modulation depth is shown in the top panel. The middle panel shows a partial view of the amplitude spectrum of the SSAEP responses for a multiple SSAEP stimulus that contains FM test signals having 20% frequency modulation depth and the bottom panel shows the SSAEP responses for a multiple SSAEP stimulus that contains IAFM test signals. The frequencies of the SSAEP responses are indicated by inverted triangles. FIG. 6b shows the corresponding polar plots for each of the SSAEP responses. The circles represent the confidence limits of each SSAEP response. If the circle does not contain the origin, then the SSAEP response can be considered to be statistically significantly (p<0.05) different from the background noise and therefore detected. The SSAEP responses in the bottom panel tend to be slightly smaller in amplitude than those obtained when only one type of modulation was used in the SSAEP stimulus. However, the phases between the SSAEP responses in the bottom panel and the corresponding responses in the top and middle panels are quite similar. Thus, IAFM stimuli allow for the independent testing of the parts of the auditory system that respond to amplitude modulation and the part of the auditory system that responds to frequency modulation. The separate SSAEP responses (i.e. in response to either an AM or FM SSAEP stimulus) can be used to evaluate hearing for a particular frequency region by incorporating both of these SSAEP responses to evaluate if a SSAEP response is present using the Stouffer method.

Experimental results have also shown that FM SSAEP stimuli can evoke SSAEP responses when the frequency modulation depths as little as 2% are used. Furthermore, SSAEP responses can be evoked when using faster FM modulation rates. Experimental data has also shown that SSAEP responses to FM stimuli could be elicited at these rapid rates and low modulation depths while producing a different phase as compared to the SSAEP response to an AM SSAEP stimulus. This suggests that the FM SSAEP stimulus was being processed differently than the AM SSAEP stimulus. This is important for testing paradigms that will rely on these faster rates. Furthermore, experimental data has shown that the use of AM and FM stimuli presented at supra-threshold intensities with depths of modulation less than 100% and rates of modulation over 70 Hz evoke SSAEP responses whose amplitudes have a correspondence to behavioral thresholds.

The signal creator 42 is also adapted to create a test signal comprising a carrier signal that is modulated by two modulation signals that modulate in the same manner but at different modulation rates. This test signal may be called a dual modulation signal. For instance, there may be 2 modulation signals which amplitude modulate a carrier signal at different modulation rates. An SSAEP stimulus based on this type of test signal may be useful in certain situations. For instance, the two SSAEP responses that are evoked by the dual modulation SSAEP stimulus can be evaluated using the Stouffer Method. Additionally, it may be useful to set the lower modulation rate in the 30–40 Hz range while the higher modulation rate is in the 70–90 Hz range. Accordingly, by using the Stouffer method, responses for both the 30–40 Hz and 70–90 Hz ranges can be simultaneously assessed. If a subject is alert, the SSAEP responses to lower modulation rates will become significant faster, while a subject that begins to doze off may cause the SSAEP responses to the faster stimuli to become significant faster.

The Stouffer method statistically compensates for trying to detect 2 rather than 1 response, however, a potential drawback may occur when an SSAEP response that is highly significant when evaluated independently fails to reach significance when assessed in concert with another SSAEP response. For example, an 80 Hz SSAEP response that is highly significant should not be assessed as being not significant if it is combined with a 40 Hz SSAEP response that is far from being significant. The software program 40 can compensate for this by using Bonferroni corrections or by allowing the user to choose different criteria for detecting an SSAEP response (i.e. choosing the p<0.01 or p<0.001 criteria instead of the p<0.05 criteria).

One possible use of the dual modulation test signal may be to monitor the level of arousal for a patient who is subjected to anesthesia. The use of anesthesia will reduce the amplitude of the 40 Hz SSAEP response but not the amplitudes of the higher frequency SSAEP responses. Thus, to ensure that the measurement of data is not contaminated by some peripheral dysfunction, such as the earphone not working correctly or the ear developing a conductive hearing loss, it would be beneficial to monitor both the 40 Hz and 80 Hz SSAEP responses simultaneously. The 80 Hz SSAEP response could be used to demonstrate that the peripheral auditory function of the subject 60 patient is normal. Another use for the dual modulation test signal is in the assessment of the ability of the subject 60 to process temporal modulation functions (as is discussed in greater detail below).

The signal creator 34 creates the various test signals which are used in the SSAEP stimulus according to Equation 2. Accordingly, Equation 2 can be used to create AM, FM, MM, OVMM and IAFM test signals.

$$s(i) = a[1 + m_a \sin(2\pi f_{am} ti)] \sin(2\pi f_c ti + F(i))/(1 + m_a^2/2)^{1/2} \quad (2)$$

where:

$$F(i) = (m f_c/(2 f_{fm})) \sin(2\pi f_{fm} ti + \theta\pi/180) \quad (3)$$

i is an address in the DAC output buffer t is the DAC rate;

$\theta$ is the phase difference in degrees between the AM and FM components of the test signal s(t);

$f_{am}$ is the modulation frequency for amplitude modulation; and, $f_{fm}$ is the modulation frequency for frequency modulation.

The test signal s(t), consists of sinusoidal tones having a carrier frequency of $f_c$. The AM is performed by the terms within the square brackets. The AM test signals are created by modulating the amplitude (a) of the carrier signal. The amplitude modulation depth is ($m_a$) controls the influence of the modulation signal on the envelope of the carrier signal.

The FM test signal is formed by modulating the phase of the carrier waveform according to the function F(i) shown in equation 3. The frequency modulation depth ($m_f$) is defined as the ratio of the difference between the maximum and minimum frequencies in the frequency modulated signal compared to the carrier frequency. For example, when a 1000 Hz carrier tone is frequency modulated with a depth of 25%, the frequency varies from 875 Hz to 1125 Hz which is a deviation ±12.5% from the carrier frequency of 1000 Hz. The term $m_f f_c/(2 f_{fm})$ represents the frequency modulation index (often denoted by $\beta$). The final divisor in equation 2 is used to maintain a constant root-mean-square amplitude for various amounts of amplitude-modulation.

If $m_f$ equals zero, then the test signal s(i) becomes an AM sinusoid. If $m_a$ equals zero, then the test signal s(i) becomes an FM sinusoid. If $f_{am}$ and $f_{fm}$ are equal and if both $m_a$ and $m_f$ are greater than zero, then the test signal s(i) becomes an MM test signal. If $f_{am}$ and $f_{fm}$ are not equal and if both $m_a$ and $m_f$ are greater than zero, the test signal s(i) becomes an IAFM test signal.

The signal creator 42 can also create a test signal in which the envelope of the signal is modulated by an exponential modulation signal. In order to use exponential amplitude modulation, the formula for AM (in the square brackets) of Equation 3 becomes:

$$\lfloor 2m_a((((1+\sin(2\pi f_m ti))/2)^{eam} - 0.5) + 1) \rfloor \quad (4)$$

where eam is the exponent. In this equation, the test signal is adjusted to maintain the same root-mean-square value for the intensity of the resulting SSAEP stimulus regardless of the exponent used in the exponential modulation signal. In order to form an FM test signal with an exponential envelope, a running integral of the envelope equation must be maintained. The running integral sums all the envelope values up to the present address in the buffer according to:

$$\varsigma_i = \sum_{1}^{i} x_i \quad (5)$$

and the envelope that is being integrated is:

$$x_i=(2\pi m_f f_c t)(((1+\sin(2\pi f_{fm} ti))/2)^{efm}-0.5) \quad (6)$$

where efm is the exponent for the exponential modulation signal. The integrated value is then inserted into Equation 3 instead of the value F(i). In addition, changes in the phase of the envelope may be made by shifting the function in time.

Referring to FIGS. 7a–7d, the usage of exponential envelope modulation for both AM and FM SSAEP stimuli produce larger responses than AM SSAEP stimuli. FIGS. 7a and 7b show the percent increase in response amplitude when using AM SSAEP stimuli with exponential envelopes compared to AM SSAEP stimuli without exponential envelopes for a 50 dB pSPL and 30 dB pSPL stimulus intensity. FIGS. 7c and 7d show response amplitudes in nV corresponding to the data shown in FIGS. 7a and 7b. At 50 dB pSPL the exponential envelope modulation increases the SSAEP response amplitude in the lower and higher frequency ranges. At 35 dB pSPL, the exponential envelope modulation increases the SSAEP response amplitude especially for the lower frequencies.

An informal analysis of the results shown in FIGS. 7a–7d indicates that using a sinusoidal signal to the power of 2 or 3 at stimulus intensities of 30 and 50 dB pSPL provides the larger SSAEP response amplitudes. Alternatively, fractional exponents may also be used. It should be noted that an increase in SSAEP response amplitude by 40% will enable the test time to be reduced by a factor of 2 when detecting the SSAEP response since the EEG noise decreases with the square root of the data (i.e. $1.4142=(2)^{1/2}$). Thus, modulating the envelope of the SSAEP stimulus with an exponential signal may result in a reduction of test time.

Exponential envelopes may also be created using AM depths below 100%, such as 80%, in order to more closely maintain the steady-state nature of the SSAEP stimulus. Additionally, the use of exponential envelopes tends to increase the amplitude of the SSAEP responses at harmonic of the modulation frequency. Accordingly, hearing tests may be utilized where envelopes are modulated by an exponential sinusoid in the 40 Hz range and the SSAEP responses are evaluated at the second harmonics of the modulation frequency. A detection method may also be devised in which the sensed EEG data is evaluated at both the modulation frequency and the second harmonic of the modulation frequency using the Stouffer method or a Stouffer method which defaults to the evaluation of a single harmonic when one of the two harmonics meets some criteria (i.e. $p<0.01$ or $p<0.001$).

Audiometric Testing Using Steady-state Evoked Potentials

The objective audiometric test apparatus 10 is also adapted to perform various audiometric tests in an objective manner using SSAEP stimuli without any necessary user control other than the selection and initiation of a particular audiometric test. Testing is objective in the sense that the subject does not have to subjectively respond to the stimuli used in the test and the individual conducting the test does not have to subjectively interpret the recorded data since statistical methods are used to analyze the recorded data. Thus, the "completely objective auditory testing system" (i.e. COATS) performs these tasks objectively. The objective audiometric test apparatus 10 may be used to evaluate hearing in subjects with normal hearing, cochlear hearing loss or abnormal auditory nervous systems, and in subjects who use hearing aids.

In general, the objective audiometric test apparatus 10 presents SSAEP stimuli, records EEG data and determines whether SSAEP responses are present in the EEG data. The objective audiometric test apparatus 10 then presents further SSAEP stimuli to obtain more precise information. However, the individual performing the audiometric tests can make decisions about which SSAEP stimuli to present and the duration of each test.

The objective audiometric test apparatus 10 is further adapted to obtain multiple audiometric thresholds concurrently. In addition, the objective audiometric test apparatus 10 is adapted to perform audiometric testing on subjects with aided and unaided hearing. With respect to aided hearing tests, the objective audiometric test apparatus 10 can be used to adjust the various parameters of a hearing aid. The objective audiometric test apparatus 10 can also perform latency tests, AM/FM discrimination tests, rate sensitivity tests, aided hearing tests, depth sensitivity tests and supra-threshold tests.

The objective audiometric test apparatus 10 also utilizes one of the databases of normative data, stored in the master database 52, to construct SSAEP stimuli, detect SSAEP responses and determine whether detected SSAEP responses are indicative or normal or abnormal hearing. The databases contain data which is correlated by subject characteristics such as age, sex and state over a variety of stimulus characteristics such as type of modulation, type of modulation envelope, modulation rate and modulation depth, etc. The database also contains data about SASEP responses such as latency, the ratio of amplitudes of SSAEP responses to AM and FM SSAEP stimuli, etc.

The objective audiometric test apparatus 10 can perform audiometric tests to assess the supra-threshold hearing of a subject. The supra-threshold tests comprise assessing the threshold of a subject's auditory system in detecting changes in the frequency or intensity of a stimulus at supra-threshold stimulus intensities. Accordingly, the supra-threshold test comprises an intensity limen and a frequency limen. The intensity limen test protocol involves varying the intensity of a stimulus by varying the AM depth. In particular, the intensity limen involves estimating the threshold for detecting a change in the amplitude modulation depth of the stimulus. The frequency limen involves varying the frequency content of the SSAEP stimulus by varying frequency modulation depth. In particular, the frequency limen involves estimating the threshold for detecting a change in the FM depth of an SSAEP stimulus. The intensity and frequency limens correlate with the subject's 60 ability to discriminate supra-threshold sounds of various intensities and frequencies.

The procedure for determining the intensity limen preferably involves the following steps:

a) Constructing an SSAEP stimulus with an AM component having an AM depth of 100%;

b) Recording the EEG data while presenting the SSAEP stimulus to the subject 60;

c) Analyzing the EEG data to determine if there was a response to the SSAEP stimulus;

d) If there is a response, then decreasing the AM depth of the AM component by half and repeating steps (b) and (c); and, e) if no response is detected then the intensity limen is determined as the lowest AM depth which resulted in an SSAEP response being detected.

Likewise, the frequency limen can be conducted according to the following steps:

a) Constructing an SSAEP stimulus having an FM component with an FM modulation depth of 40%;
b) Recording the EEG data while presenting the SSAEP stimulus to the subject;
c) Analyzing the EEG data to determine if there was an SSAEP response to the SSAEP stimulus;
d) If there is a response, then decreasing the FM depth of the FM component by half and performing steps (b) and (c); and,
e) if no response is detected then the frequency limen is determined as the lowest FM depth which resulted in an SSAEP response being detected.

The supra-threshold hearing test may further involve varying the modulation depths in an SSAEP stimulus and examining the size of the resulting SSAEP responses compared to population normative values.

The supra-threshold hearing test may further comprise a method which should be less prone to inter-subject differences. The method comprises measuring the amplitude of the SSAEP response when presenting the subject with an AM SSAEP stimulus that has an AM depth of 100%. This response amplitude may then be compared to SSAEP response amplitudes that are obtained when presenting the subject with an AM SSAEP stimulus that has smaller AM depths. Accordingly, a demonstrative measure may be the ratio of the amplitude of an SSAEP response which is recorded while presenting a subject with an AM SSAEP having a 50% AM depth to the amplitude of an SSAEP response obtained while presenting a subject with an AM SSAEP having a 100% AM depth. As in the case of absolute amplitudes, normative values can be obtained for these ratios using appropriate age and sex matched control populations that were exposed to similar stimuli. These normative values can be obtained from one of the databases in the master database 52.

The objective audiometric test apparatus 10 may also perform latency tests on the subject to determine if the subject has normal or abnormal hearing. Through the use of a "preceding cycles technique", experiments have shown that SSAEP responses have reliable and repeatable latency values in normal healthy ears. The latency values are obtained from the phases of the detected SSAEP responses. The latency of an SSAEP response is important for diagnosing various kinds of sensorineural hearing loss. An abnormally long latency value may indicate that an acoustic neuroma is present. Alternatively an abnormally short latency value may indicate that the subject has Meniere's disorder.

Figure 8:
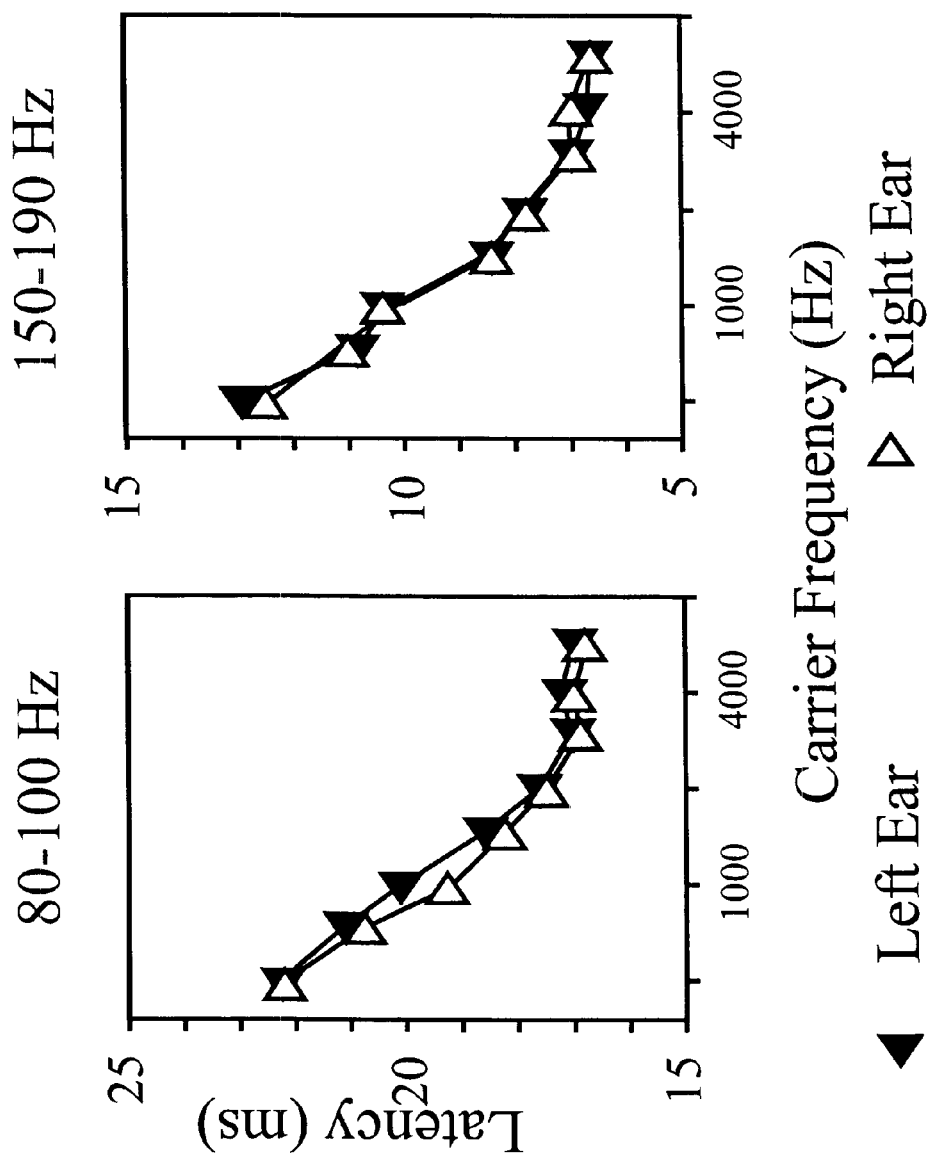
FIG. 8 is a pair of graphs of the latencies calculated for 80 and 160 Hz modulation rates for SSAEP responses in response to SSAEP stimuli presented to the right and left ears of a group of subjects.
Figure 9:
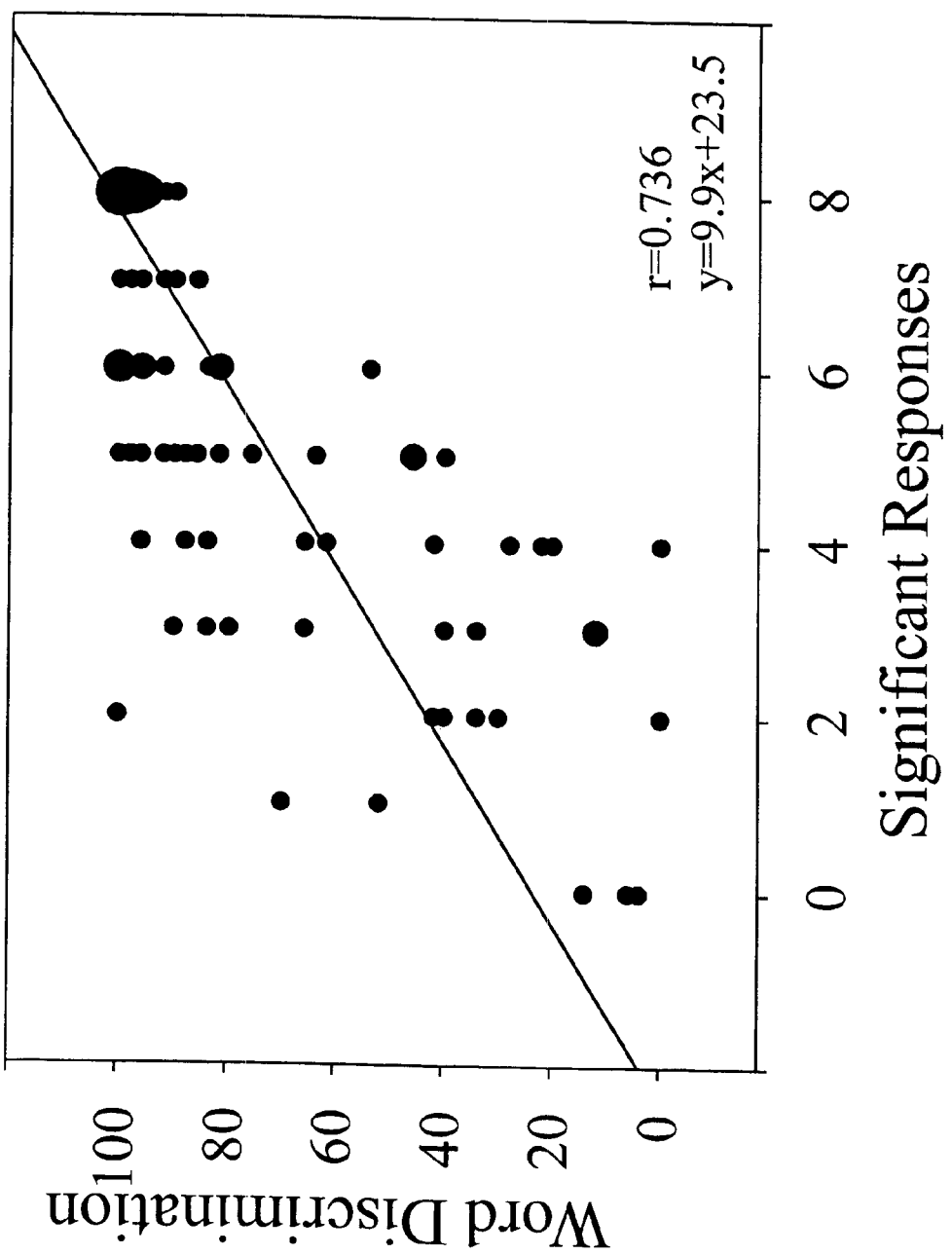
FIG. 9 is a plot of word discrimination as a function of the number of significant responses to IAFM SSAEP stimuli for various subjects.

Referring to FIG. 8, the results of a set of experiments using dichotic stimulation are shown. A multiple SSAEP stimulus with four carrier signals having carrier frequencies that were separated by an octave were presented to one ear and four stimuli at intervening carrier frequencies were presented to the other ear for a group of subjects. The SSAEP stimuli were then reversed and applied to the opposite ear. The data shown in FIG. 9 are the latencies derived by modeling the vector-averaged phase delays measured across eight subjects in the subject group. These phase delays were measured as having occurred after 1 preceding cycle in the stimulus waveform. Phase delay was found to be similar for SSAEP responses evoked by SSAEP stimuli having one test signal component or SSAEP stimuli having more than one test signal component, as long as adjacent carrier frequencies in the SSAEP stimulus were separated by at least 1 octave. The experimental results showed that phase (and hence latency) are stable over time and change as expected with the intensity level of the stimulus. Phase delay was also the same for monaural and binaural presentation.

Since phase delay was found to be consistent, a normative database, stored within the master database 52, containing appropriate age and sex matched normative phase delay or latency values for various stimuli may be constructed. This normative database of phase delay values may then be used as a reference to detect abnormalities in subjects by measuring their phase delay or latency. In addition to absolute latency values, normative values for the differences between the latencies for responses to pairs of stimuli may be useful in the detection of abnormal hearing. For instance, the difference between the latency estimate for SSAEP stimuli with 2000 and 4000 Hz carrier frequencies may be used.

The procedure for measuring latency uses the following steps:

a) Record the steady-state response to an SSAEP stimulus and measure the onset phase of the response in degrees;
b) Convert the onset phase to a phase delay (P) by subtracting it from 360° (it may be necessary to make the phase delays 'rational' across different carrier frequencies, i.e. an extra 360 degrees may be added to the phase delay (i.e. phase unwrapping) so that the phase delay for a carrier frequency with a lower frequency is longer than the phase delay for a carrier frequency with a higher frequency, (a situation which makes sense since higher frequencies are transduced near the basal end of the cochlea)); and,
c) Convert the phase delay to a latency (L) value in milliseconds according to the formula:

$$L=1000*(P+N*360)/(360*f_m) \quad (7)$$

where $f_m$ is the modulation frequency for the SSAEP stimulus that evoked the SSAEP response and N is chosen as the number of preceding cycles. For modulation frequencies in the range of approximately 75–100 Hz, N can be chosen to be 1. The value of N can be determined from normative studies using different modulation frequencies. N is set for each response in order to bring the latency values calculated for a subject as close as possible to normative latency values.

Another way of determining the latency value is to present an SSAEP stimulus at a given carrier frequency and vary the modulation frequency. The phase of the response to each different modulation frequency is then measured and plotted versus modulation frequency. The latency value is then estimated from the slope of the phase versus modulation frequency plot.

The objective audiometric test apparatus 10 can also perform AM/FM discrimination tests using SSAEP stimuli. The AM/FM discrimination tests correlates with speech discrimination tests. One test involves using the number of responses to multiple IAFM SSAEP stimuli as an estimate of the ability of a subject's auditory system to discriminate the frequencies and intensities necessary for speech perception. If the SSAEP responses suggest that the auditory system of the subject cannot make these discriminations then the subject will not be able to discriminate all of the words. Accordingly, the intensity of the SSAEP stimulus would be similar to the intensity at which words would be presented during a subjective speech discrimination test in terms of root mean square SPL.

Referring to FIG. 9, the percentage of words that were correctly discriminated by a subject versus the number of significant SSAEP responses that were detected when a multiple IAFM SSAEP stimulus was presented to the subject is shown. The multiple IAFM SSAEP stimulus comprised AM and FM signals with carrier frequencies of 500, 1000, 2000 and 4000 Hz. The areas of the plotted circles are related to the number of data points, with the largest circle representing 7 data points. This scattergram shows a correlation between the number of detected (i.e. significant) SSAEP responses and the word discrimination. The IAFM stimulus may be a good stimulus for looking at word discrimination since it presents multiple AM and FM stimuli simultaneously. Other multiple stimuli may also be used. For example, eight separate carrier signals may be presented with four of these amplitude-modulated and the other four frequency-modulated. The idea is to evaluate both amplitude and frequency discrimination at multiple frequencies.

Accordingly, a test protocol that could be used to indicate the speech processing ability of the subject may consist of determining the number of SSAEP responses that were evoked by a multiple IAFM SSAEP stimulus. The test period may persist for a certain amount of time, for example 12 minutes, or until the residual noise background reached a minimal limit. The testing may be done both in the absence and presence of noise masking as is conventionally done in subjective speech discrimination tests. The use of noise masking is important in testing subjects who have difficulty listening to speech with background noise. The word recognition score is then be estimated from a function that correlates the number of detected SSAEP responses which were evoked by the multiple IAFM SSAEP stimulus to the word recognition score. The actual function may be determined from studies on a normative sample population of subjects. Control recordings need to be included to ensure that responses can be reliably recorded (and that the noise levels are not too high). These control tests may employ SSAEP response to single tones (i.e. sinusoids) with 100% amplitude modulation.

The AM/FM discrimination test could further comprise testing the ability of the subject to discriminate frequency changes from amplitude changes. The amplitude of the SSAEP response to an FM component of an IAFM SSAEP stimulus could be compared to the amplitude of the SSAEP response to an AM component of an IAFM SSAEP stimulus in the form of a response amplitude ratio (denoted by FM/AM). Alternatively individual FM SSAEP and AM SSAEP stimuli may be used. This FM/AM ratio can then be compared to normative FM/AM ratios that may be computed for all age groups and stored in a database within the master database 52. Initial studies suggest that FM/AM ratios for 500 to 6000 Hz carrier frequencies are between approximately 1 and 2 for younger subjects and below approximately 1 for older subjects. Deviations from this range may be used to indicate a problem in the part of the auditory system that processes AM signals or the part of the auditory system that processes FM signals.

The objective audiometric test apparatus 10 can also perform rate sensitivity tests in which the amplitude of the SSAEP response to an SSAEP stimulus with increasing modulation frequencies may be measured. The various SSAEP stimuli that have been discussed (i.e. AM, FM, OVMM, MM, IAFM) and the use of exponential envelope modulation can be presented with modulation rates that vary from a few Hz to several hundred Hz. In general, as the modulation frequency (or modulation rate) increases, the amplitude of the SSAEP response to the SSAEP stimulus decreases with the exception of local maxima that can occur in the 40, 80, and 160 Hz ranges. However, this rate of response amplitude decrease can vary for different subjects, particularly if the different subjects include individuals with normal hearing and abnormal hearing.

Figure 10:
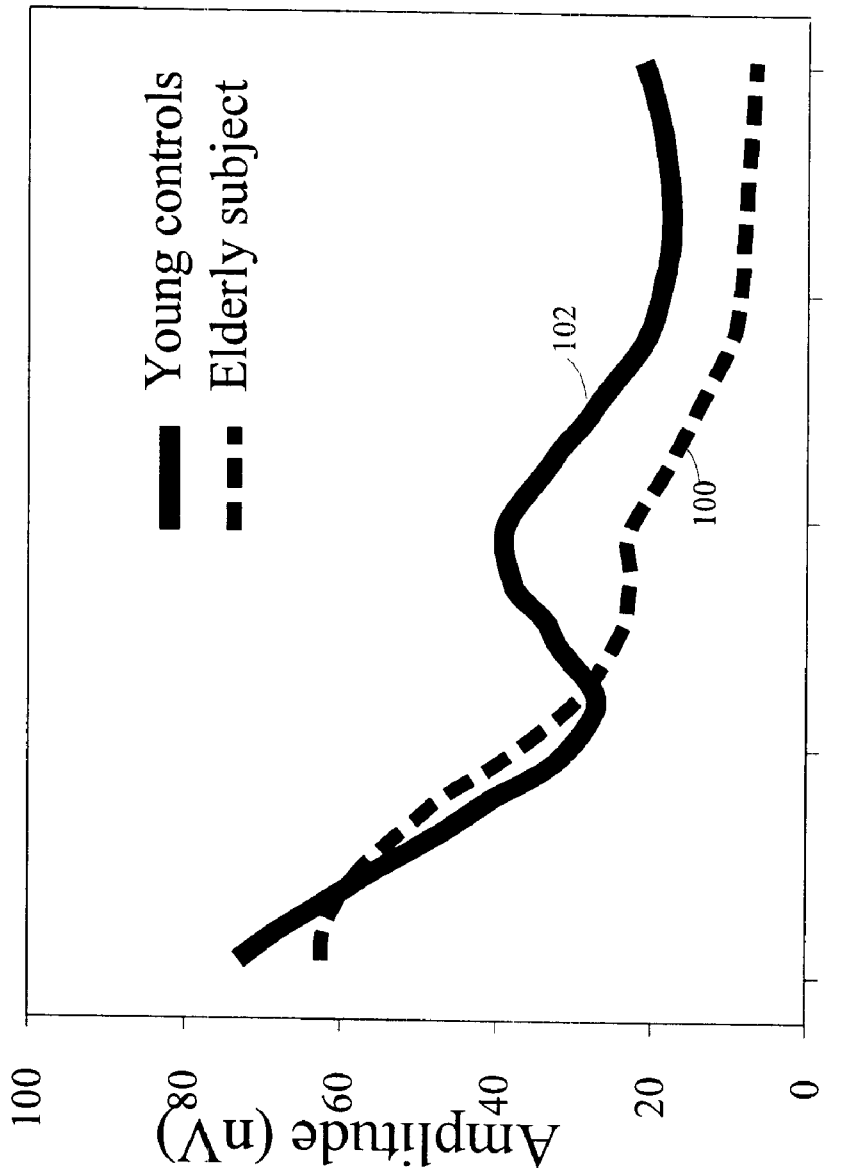
FIG. 10 is a graph of amplitude of SSAEP responses as a function of SSAEP stimulus modulation rate for a group of young control subjects and for an older subject with minor hearing loss.

Referring to FIG. 10, the SSAEP response amplitudes of an older subject 100 measured in response to SSAEP stimuli having a range of modulation frequencies is compared to the average SSAEP response amplitudes obtained from a group of normal control subjects 102. The data shows that the decrease in SSAEP response amplitude with increasing modulation rate occurs more rapidly for the older subject 100 who also had a minor hearing loss. Although the older subject 100 could hear the SSAEP stimuli with higher modulation frequencies, the SSAEP response amplitudes for the SSAEP stimuli with higher modulation frequencies did not produce large amplitude SSAEP responses. Therefore, by comparing the rate of decrease in the SSAEP response amplitude (i.e. the rate sensitivity) that occurs with increasing SSAEP stimuli with increasing modulation rates to those obtained from an appropriate normative population, subjects with abnormal hearing can be detected. Alternatively, instead of using the absolute value of the SSAEP response amplitude (which is shown in FIG. 10), a ratio of SSAEP response amplitudes may be used such as the ratio of the SSAEP response amplitude for an SSAEP stimulus with a low modulation frequency to the SSAEP response amplitude for an SSAEP stimulus with a high modulation frequency.

The larger decay in SSAEP response amplitude that occurs with increasing modulation frequency in the older subject (with a minor hearing loss) is similar to the decay that would be predicted by studies on older adults who display large gap detection thresholds and more rapid decay in their temporal modulation transfer functions. Since an AM SSAEP stimulus with a carrier frequency of 100 Hz can be considered similar to a stimulus which is on for half a cycle and off for half a cycle then a 100 Hz AM SSAEP stimulus may be considered similar to having a stimulus on time of 5 msec and a gap duration of 5 msec. Additionally, an AM SSAEP stimulus with a 200 Hz carrier frequency is similar to having a stimulus "on" time of 2.5 msec, with a gap duration of 2.5 msec. Accordingly, the SSAEP responses which are recorded in response to SSAEP stimuli with modulation frequencies in the range of 100 to 200 Hz may be used to provide a physiological correlate of the modulation transfer function or the gap function of an individual for gaps ranging from 5 msec to 2.5 msec. The period of the gap of the SSAEP stimulus may be functionally increased by decreasing the modulation frequency or by increasing the exponent when using an exponential modulation signal with the SSAEP stimulus. Alternatively, both of these operations may be applied to the SSAEP stimulus.

The rate sensitivity test may further comprise using a multiple SSAEP stimulus comprising 4 AM test signals. The modulation frequencies of the 4 AM test signals can initially be chosen to be 40, 44, 48, and 52 Hz for example. If the two ears of a subject have been shown to have similar hearing ability, then the other ear of the subject may be presented with a multiple SSAEP stimulus that comprises 4 AM test signals with modulation frequencies of 42, 46, 50, and 54 Hz. After each recording is done, the modulation frequency of each AM test signal may be increased by 10 Hz. In this manner, estimates of SSAEP response amplitude may be measured in 10 Hz steps from approximately the 40 to 190 Hz range. A plot of SSAEP response amplitude versus modulation frequency may then be generated for each of the AM test signals or for a combination of the SSAEP responses to the 4 AM test signals such as the mean SSAEP response amplitude at each modulation frequency. If the mean values at each of the modulation frequencies are found to be more useful than using information obtained for each of the 4 AM tones separately, then single rather than multiple stimuli may be used in this test. Alternatively, the carrier waveform could be band-limited noise that is modulated at a single modulation rate. Since broadband noise can evoke a larger SSAEP response than that evoked by a single AM tone, the duration of this test should be shorter.

The objective audiometric test apparatus 10 may further estimate a threshold above which the auditory system of a subject no longer responds to the modulation frequency used in the SSAEP stimulus. This test yields a "cutoff" modulation frequency threshold at which the auditory system of the subject no longer recognizes SSAEP stimuli with higher modulation frequencies.

The objective audiometric test apparatus 10 may also be used with subjects who have hearing aids. In this case the objective audiometric test apparatus 10 may be used to adjust the settings (e.g. gain) of the hearing aid so that the subject can hear sounds near his/her threshold. The adjustment protocol comprises presenting the subject with an SSAEP stimulus while recording the EEG of the subject. The EEG is then analyzed to determine if an SSAEP response to the SSAEP stimulus occurred. If an SSAEP response did not occur, then the gain of the hearing aid may be increased in step changes until an SSAEP response to the SSAEP stimulus can be detected (or until some maximum level of gain is reached which is necessary to prevent the use of any gain levels which may damage the ear). Typically, this protocol would use SSAEP stimuli with an intensity level similar to that of conversational speech which may be approximately 50–60 dB HL. The SSAEP stimuli would also use modulation depths that are typical of speech sounds such as FM test signals having an FM depth of approximately 20% and AM test signals having an AM depth of approximately 50%.

Depending on the parameters that can be adjusted in the hearing aid, the adjustment protocol can be made more or less specific in its operations. For example, the gain of the hearing aid may be adjusted separately for different frequency regions. Therefore, these gains may be separately and concurrently adjusted. Alternatively, if only the gain and the filter slope of the hearing aid can be adjusted then a different adjustment protocol may be used to adjust these parameters on the basis of the recognized SSAEP responses when presenting SSAEP stimuli at different frequencies to the subject.

The objective audiometric test apparatus 10 may further include another hearing aid adjustment protocol known as the Seek and Adjust Single-Multiple (SASM) technique. In this case, the gain of the hearing aid is automatically increased, by the objective audiometric test apparatus 10, until an SSAEP response to an SSAEP stimulus is detected. After this has been done for all the SSAEP stimuli, several paired SSAEP stimuli may then be presented to the subject. Alternatively, rather than pairs, four or more AM test signal may be used in the multiple SSAEP stimulus. This is done because it has been shown that the thresholds for a multiple SSAEP stimulus (which may be more similar to natural sounds such as speech) may be higher than the thresholds for SSAEP stimuli having comprising single test signals. For example, in the case of a high frequency hearing loss that is steeply sloping near 4 kHz, both a 2 kHz and a 4 kHz AM sinusoid may be presented together in a multiple SSAEP stimulus. If a 60 dB SPL stimulus needed to be amplified by 20 dB in order for the auditory system of the subject to detect the 2 and 4 kHz AM test signals, then the multiple AM SSAEP stimulus may first be presented to the subject using a 20 dB gain. If a significant SSAEP response is not obtained for either component of the multiple SSAEP stimuli, the gain for this frequency region in the hearing aid may be increased a maximum of 3 times in +5 dB SPL steps for example. If, on the other hand, a significant SSAEP response is not obtained for either component of the multiple SSAEP stimulus, then the gain of the hearing aid corresponding to the frequency region of either the first component of the multiple SSAEP stimulus, or the second component of the SSAEP stimulus, or both components of the SSAEP stimulus may be increased a maximum of 3 times in +5 dB SPL steps (for example). In this manner, interactions can be evaluated, and the gain parameters that result in the lowest overall gain will be automatically chosen for the hearing aid.

The objective audiometric test apparatus 10 may also be used to objectively measure the audiometric thresholds of a subject by presenting multiple SSAEP stimuli at multiple stimulus intensities to the subject and recording the SSAEP responses. The objective audiometric test apparatus 10 may then adjust the intensity levels of the SSAEP stimuli based on the detection of SSAEP responses and the amplitude of the SSAEP responses. Since a multiple SSAEP stimulus may be used, multiple audiometric thresholds may be estimated simultaneously. Experimental results have shown that audiometric threshold estimated with SSAEP stimuli are correlated with behavioral audiometric thresholds.

The objective audiometric threshold assessment method involves using a multiple SSAEP stimulus comprising 4 or more AM SSAEP test signals having an amplitude modulation depth of 100% and carrier frequencies that are separated by at least one-half octave. Alternatively, the multiple SSAEP stimulus may comprise FM test signals each having an FM modulation depth in the range of 20%. The use of these modulation depths for the AM and FM components of the multiple SSAEP stimulus permit the audiometric testing to be frequency specific. The SSAEP stimulus may also comprise MM or OVMM SSAEP test signals having similar modulation depths. Furthermore, the SSAEP stimulus could also have an envelope that is modulated by an exponential modulation signal with the modulation being done such that the resulting SSAEP stimulus is predominantly frequency specific.

The objective audiometric threshold assessment method may further involve adjusting the intensity of each component of the multiple SSAEP stimulus either independently or simultaneously. In the independent case, the intensity of a component of the multiple SSAEP stimulus is reduced when the corresponding SSAEP response has been detected in the recorded EEG data. This independent intensity adjustment can be achieved if each component of the multiple SSAEP stimulus is sent to a separate DAC that can be adjusted in real time. Alternatively, the components of the multiple SSAEP stimulus may be combined digitally and then presented through 2 DACs (1 for each ear of the subject). In this case, the intensity of a given component of the multiple SSAEP stimulus may be digitally adjusted independently of the other components and combined in the multiple SSAEP stimulus. This may be done provided that the DAC has sufficient resolution (e.g. 16 or more bits) to allow for the accurate presentation of less intense components in the presence of higher intensity components.

To illustrate this principle, a multiple SSAEP stimulus may comprise 4 AM test signals with carrier frequencies of 0.5, 1, 2, and 4 kHz presented at 50 dB SPL. Each of the 4 test signals are represented in a 16 bit buffer with about 16,384 bits each (this of course depends on the particular data acquisition board that is used in the test apparatus). If the SSAEP response to the AM test signal with a carrier frequency of 1 kHz becomes significant first, in order to present this AM test signal at 40 dB SPL while the other test signal components are presented at 50 dB SPL, the test signal must be decreased by 10 dB SPL. Since the multiple SSAEP stimulus is stored in the RAM of the processor 12, a new multiple SSAEP stimulus may be created by adding together the test signal components (now with a reduced intensity AM test signal component having a 1 kHz carrier frequency), and sent to the output buffer of the DAC 16. In this case, a dual buffer technique can be used in which the output buffer can be originally defined as being twice as long as an SSAEP stimulus. The multiple SSAEP stimulus is then loaded into the first half of the buffer. When a new multiple SSAEP stimulus is created, it can be loaded into the second half of the output buffer, such that when the end of the first buffer is reached, the new multiple SSAEP stimulus can be seamlessly presented to the subject by simply changing the memory address where the DAC 16 looks for data to convert into analog data.

Alternatively, rather than recreating the entire multiple SSAEP stimulus, the intensity of a single component within the multiple SSAEP stimulus may be adjusted using the Stimulus Flux method. The Stimulus Flux method involves changing the intensity of a single component within the multiple SSAEP stimulus by creating and separately storing a waveform for each component of the multiple SSAEP stimulus. When the intensity of a particular component of the multiple SSAEP stimulus must be adjusted, the amplitude of the corresponding waveform is multiplied by the required amplitude factor such that when this waveform is subtracted from the multiple SSAEP stimulus, the intensity of the desired component will be adjusted to the desired value. The new multiple SSAEP stimulus may then loaded into the output buffer of the DAC 16 and subsequently presented to the subject 60.

Figure 11:
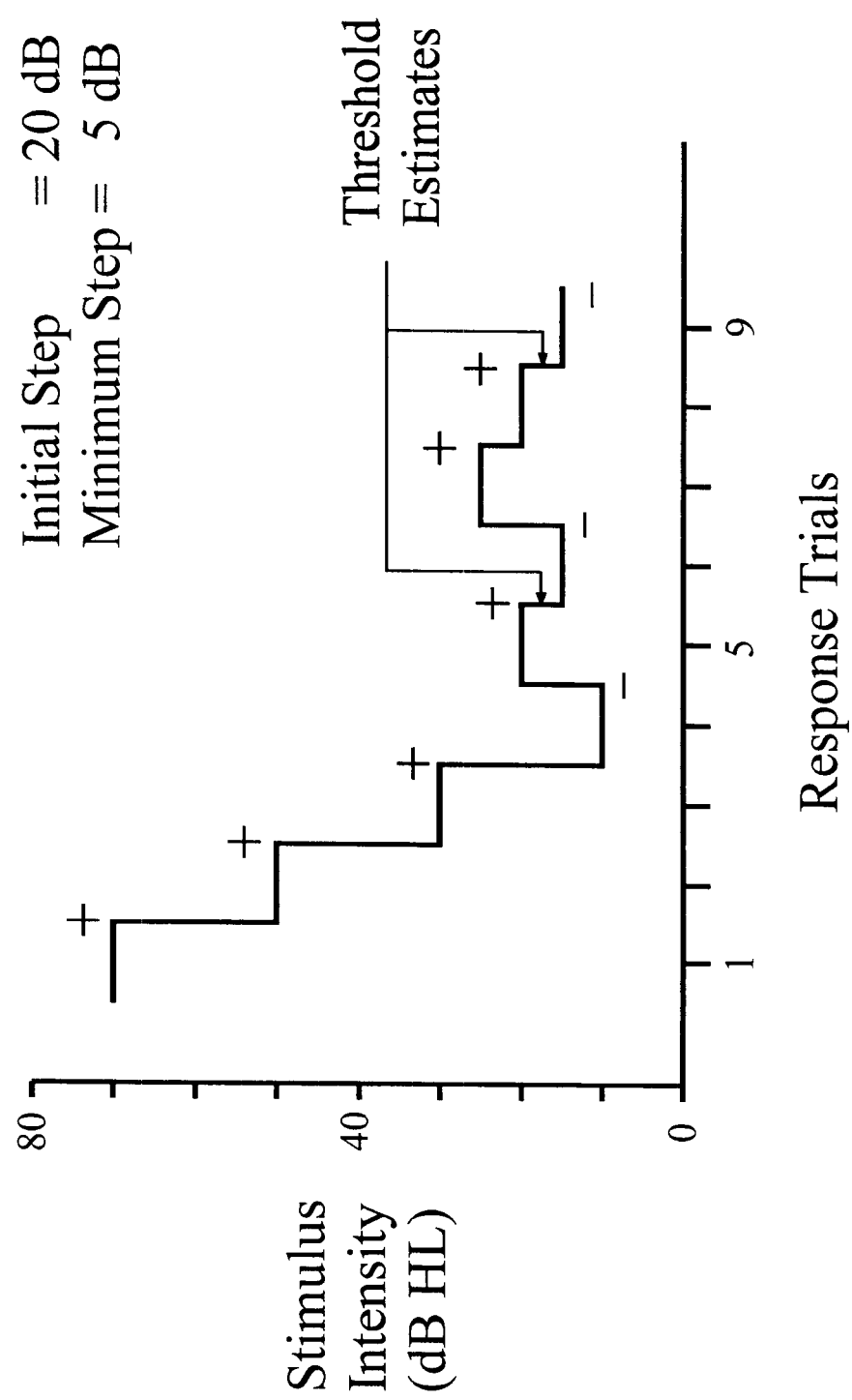
FIG. 11 is a schematic diagram of how an audiometric threshold can be estimated using an algorithm that automatically adjusts sound intensity on the basis of whether an SSAEP response is detected.

An algorithm to carry out the objective audiometric threshold assessment method may involve an adaptive staircase method. The adaptive staircase method is designed to bracket the audiometric threshold as efficiently as possible by adjusting the value of a step size. The step size is used to increase or decrease the intensity of components within the multiple SSAEP stimulus during subsequent presentations of the multiple SSAEP stimulus to the subject. The step size may be adjusted on the basis of SSAEP response detection at a given stimulus intensity and the sequential replication of the audiometric threshold estimates. One possible definition of the audiometric threshold may be the intensity of a particular component (for which the audiometric threshold is being determined) of the multiple SSAEP stimulus between the last two stimulus intensities which resulted in detected and not detected SSAEP responses when using a minimum step size. The audiometric thresholds may be then confirmed based on replicated audiometric threshold estimates using the staircase procedures shown in FIG. 11.

The objective audiometric threshold assessment method also includes the selection of initial stimulus intensity, initial step-size and minimum step-size. Maximum and minimum limits for the stimulus intensities must also be set above and below which the method will not look for audiometric thresholds. The rules for step size changes may also be defined. Furthermore, the step-size itself may decrease with time or vary with the remaining range of stimulus intensities that are to be tested (e.g. the step size can be defined as half of the distance between the present stimulus intensity and the minimum or maximum stimulus intensity which will be tested). There must also be a minimum step size that will determine the precision whereby the audiometric threshold is estimated (e.g this may be 5 or 10 dB SPL). Other parameters that need to be set are the criteria whereby an SSAEP response is judged to be present or absent. The Phase weighted t-test or the phase zone method may be used to detect the response. Alternatively, any detection method known in the art may be used. The criterion for judging that an SSAEP response to an SSAEP stimulus is absent may be adjusted based on a minimum level of residual background noise in the processed EEG data. This criterion may also include a time limit for which the test expires. Alternatively, both of these criteria may be used.

The objective audiometric threshold assessment method may be implemented as follows. Several test signals components are combined in a multiple SSAEP stimulus which is presented at a given intensity level. Alternatively, a single test signal component may be used in the SSAEP stimulus. EEG data is simultaneously recorded, while the SSAEP stimulus is presented to the subject. The recorded EEG data is subsequently analyzed for SSAEP response detection. As soon as one SSAEP response is detected, the intensity of the test signal component (denoted as TS1) which evoked this SSAEP response is reduced by a step-size equal to half the dB SPL distance between the current intensity level for the test signal component TS1 and the minimum intensity level which will be tested in the audiometric threshold test. Accordingly, a new multiple SSAEP stimulus will be constructed based on this new test signal component TS1. The method now involves the same steps as before: presenting the multiple SSAEP stimulus, recording EEG data and analyzing the data for any SSAEP responses. The protocol also involves halving the step size for the component in the multiple SSAEP stimulus that evoked a detected SSAEP response. Therefore, if an SSAEP response is detected for the test signal component TS1, then the stimulus intensity for the test signal component TS1 is reduced by the new step size. Alternatively, if a response was not detected for the test signal component TS1, then the intensity level for the test signal component TS1 is increased by the new step size. An estimate of noise level of the recorded EEG data may also be made to ensure that a lack of SSAEP response detection is not due to excessive noise in the recorded EEG data. The noise estimate may also be used as a multiplicative factor to increase the test time when presenting a given multiple SSAEP stimulus. Thus, the test time may be extended as a function of the amount of noise in the recorded EEG data.

The objective audiometric threshold assessment method further comprises obtaining threshold crossings until thresholds for all test signal components in the multiple SSAEP stimulus have been obtained. Alternatively, when a sufficient number of threshold crossings have been obtained for some test signal components in the multiple SSAEP stimulus but not for other test signal components, a new multiple SSAEP stimulus could be constructed comprising the test signal components for which thresholds have not been obtained. Testing would then continue with this new multiple SSAEP stimulus.

The objective audiometric threshold assessment method may further comprise adjusting the intensities of all of the test signal components in the multiple SSAEP stimulus simultaneously. Some test signal components of the multiple SSAEP stimulus may then be removed after a specified duration of time if SSAEP responses have been detected for these test signal components. The remaining test signal components in the multiple SSAEP stimulus are then presented for another duration of time such as 90 seconds for example. Since the detection of an SSAEP response to a single SSAEP stimulus may require about 90 seconds, this audiometric threshold detection procedure will be approximately 2 times as fast as testing with an SSAEP stimulus which has single test signal components. Additionally, since SSAEP stimuli comprising AM, FM, OVMM or MM test signals can be presented binaurally to a subject (i.e. to both ears of the subject), the objective audiometric threshold assessment method may be 4 times as fast as testing with an SSAEP stimulus comprising single test signals presented separately to each ear.

The objective audiometric threshold assessment method may alternatively present test signal components in the multiple SSAEP stimulus at different intensities. Since SSAEP responses to test signals having carrier frequencies of 500 Hz and 4000 Hz typically require more time to be detected compared to SSAEP responses to test signals having carrier frequencies of 1000 and 2000 Hz, the stimulus intensity of the former test signal components may be increased relative to the later test signal components. Accordingly, the intensity of the test signal components having 500 Hz and 4000 Hz carrier frequencies may be presented at 10 dB SPL above the intensity level for the test signal components having carrier frequencies of 1000 Hz and 2000 Hz (note that these exact frequencies do not have to be used and are shown for illustrative purposes; it is the frequency region in which they reside that is important). In this fashion, the SSAEP responses to the test signal components may all be detected at approximately the same time. Alternatively, the multiple SSAEP stimulus may comprise only 2 test signal components, such as test signal components having 500 Hz and 4000 Hz carrier frequencies since these test signals will be transduced by separate, fairly spaced apart regions of the basilar membrane and SSAEP responses to these particular stimuli will both require long times to detected.

When the objective audiometric threshold assessment method has been completed, the results can be presented in a standard audiometric format as is commonly known to those skilled in the art. The presentation of the test results may include highlighting whether SSAEP responses to test signal components were detected when the test signal components were presented alone or in combination with other test signal components. For example, these SSAEP responses may be circled or highlighted with a particular color. In addition to the actual audiometric thresholds that were obtained from testing, estimates of audiometric thresholds may also be made which are extrapolated from detected SSAEP responses for test signal components which were presented at higher stimulus intensities. For example, by taking the decrease in the amplitude of the SSAEP responses obtained for a test signal component presented at 60, 50, and 40 dB SPL, an estimate of when an SSAEP response will not be detected may be made by projecting a line connecting the amplitude of these detected SSAEP responses to the level of the average background EEG noise.

Multi-modality Testing

Figure 12:
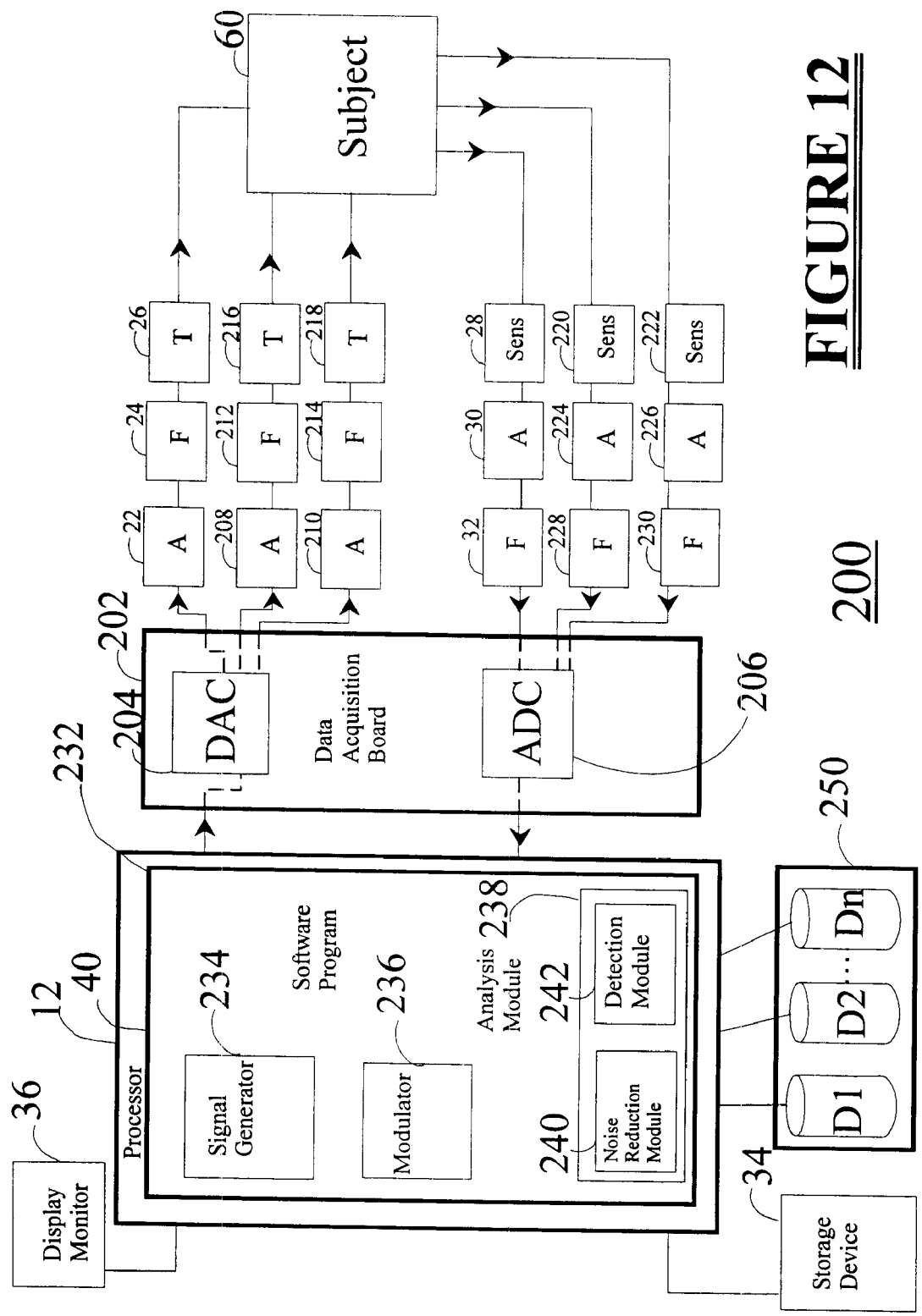
FIG. 12 is a schematic of an objective multi-modality test apparatus.

Referring to FIG. 12, an alternate embodiment of the objective audiometric test apparatus 10 comprises an objective multi-modality test apparatus 200. Please note that in FIG. 12, like numerals were used to represent elements that are similar to the elements of the objective audiometric test apparatus 10 shown in FIG. 1a. The objective multi-modality test apparatus 200 may be used to concurrently test other modalities while the auditory system of the subject 60 is being tested. In this embodiment, the visual and somatosensory modalities are concurrently tested with the auditory modality. In other embodiments, other sensory modalities may be concurrently tested with the auditory system. The testing of multiple modalities may allow for the determination of whether an auditory abnormality is part of a more widespread disorder of the nervous system such as multiple sclerosis for example. In addition, multi-modality testing may be used to investigate neurological disorders.

The objective multi-modality test apparatus 200 comprises the processor 12, a data acquisition board 202 having at least one DAC 204 and at least one ADC 206, amplifiers 22, 208 and 210, filters 24, 212 and 214, transducers 26, 216 and 218, sensors 28, 220 and 224, amplifiers 30, 224 and 226 and filters 32, 228 and 230. The processor 12 further comprises a software program 232 that encodes the functionality of the objective multi-modality test apparatus 200. The software program 232 comprises a signal creator 234, a modulator 236 and an analysis module 238 having a noise reduction module 240 and a detection module 242. The software program 232 is also coupled to a plurality of a master database 250 which comprises a plurality of databases D1 to Dn. The processor 12 is also coupled to the storage device 34 and the computer display 36.

In use, the signal creator 234 generates test signals that are appropriate as stimuli for evoking auditory, visual and somatosensory response potentials. The modulator 236 may be employed in the creation of the test signals. The test signals are then sent to the DAC 204 which may comprise a plurality of output channels or may be a plurality of single channel DACs. The DAC 204 sends the test signals to the amplifiers 22, 208 and 210. The amplifiers 22, 208 and 210 amplify the test signals to adjust the intensity level of the test signals to levels that are suitable for testing. The amplified test signals are then sent to filters 24, 212 and 214 to remove any noise from the digital to analog conversion process and the amplifying process.

The filtered, amplified test signals are then sent to the transducers 26, 216 and 218 so that the test signals may be transduced by and simultaneously presented to the subject 60. The transducer 26 may be an auditory transducer that transduces the appropriate test signal into an auditory stimulus. Accordingly, the transducer 26 may be a pair of headphones or at least one insert earphone. The particular test signals used for the auditory stimulus can be any of the stimuli that were previously discussed for the objective audiometric test apparatus 10. For instance the auditory stimulus may be two AM sinusoids (i.e. tones) at different carrier frequencies, having modulation frequencies of 87 and 93 Hz.

The transducer 216 may be a visual transducer that transduces the appropriate test signal into a visual stimulus. Accordingly, the transducer 216 may be a strobe light which can produce a pulsating flash or the transducer 216 may be a grid of light emitting diodes. The visual stimuli may be presented at modulation rates of 16 and 18 Hz, for example, to the left and right eyes of the subject 60. Alternatively, the visual stimuli may be presented to only one eye of the subject 60. As in the case of the auditory stimuli, multiple modulated visual stimuli may be presented to a single eye.

The transducer 218 may be a tactile transducer that transduces the appropriate test signal into a tactile stimulus. Accordingly, the transducer 218 may be a vibrotactile stimulator or the like. The vibrotactile stimulator may be applied to at least one finger of the subject 60. For instance, the vibrotactile stimulator may be applied to the left and right index fingers of the subject 60. The tactile stimuli may be presented at rates of 23 and 25 Hz although other presentation rates may be used.

When presenting the multi-modality stimulus to the subject 60, the test signals which are used must be chosen such that the frequencies of the responses to each of the auditory, visual and tactile stimuli are not equal to each other, are not integer multiples of each other and share a minimum of common factors. This must be ensured so that the responses and their harmonics do not interfere with one another.

EEG data is recorded while the multi-modality stimulus is presented to the subject 60. The EEG data of the subject 60 is recorded using sensors 28, 220 and 222 that are typically electrodes. These electrodes are placed on certain regions of the subject 60 to obtain EEG data with better signal to noise ratios. The sensors 220 that measure the response to the visual stimulus may be placed over the occipital regions of the brain of the subject 60. The sensors 222 that measure the response to the tactile stimulus may be placed over the central scalp which is contralateral to the presentation of the tactile stimulus. The sensors 28 that measure the response to the auditory stimulus may be placed on the vertex of the subject 60. In each of these cases alternative placements of the electrodes is possible. For instance, the placement of these sensors may also involve using a plurality of electrodes placed at numerous (i.e. 32 or 64) locations on the scalp of the subject 60.

Each of the sensed potentials (i.e the EEG data which is also understood to be a time series data) may then be amplified by amplifiers 30, 224 and 226 to an amplitude level that is sufficient for digitization. The amplified EEG data may then be filtered by filters 32, 228 and 230. The amplified, filtered EEG data is then sent to the ADC 206 for digitization at a sampling rate that is sufficient to sample the EEG data without aliasing.

The sampled data is then analyzed by the analysis module 242. The data is first preprocessed by the noise reduction module 240 to reduce the amount of noise in the sampled data and produce noise reduced EEG data. The noise reduction module 242 may use the sample weighted averaging method to reduce noise. The noise reduction module 242 may also use adaptive artifact rejection. Alternatively, the noise reduction module 242 may use any noise reduction algorithm that is known in the art.

The noise reduced EEG data is then analyzed by the detection module 242 to determine whether there are any responses present in the noise reduced EEG data. The detection module 242 may implement the phase weighted t-test, the phase zone technique or the MRC method. Alternatively, the detection module 242 may use other detection algorithms that are known in the art. The detection module 242 may also provide a probability estimate that a detected response is truly a signal and not noise. The detected responses may then be compared to normative data on other subjects which is contained in the master database 250. This comparison may provide an indication of whether the subject 60 has a widespread disorder of the neural system.

Based on the objective multi-modality test apparatus 200, a procedure for multi-modality testing would comprise the following steps:

(i) Attach electrodes to the subject 60;
(ii) Set up or attach transducers to present the multi-modality stimuli to the subject 60;
(iii) Present the multi-modality stimuli to the subject 60 wherein the stimulus for each modality is synchronized with the objective multi-modality test apparatus 200 so that the multiple responses can be recognized by their signature modulation frequencies;
(iv) Record the EEG data at each electrode location to obtain three EEG data time series;
(iv) Reduce the noise in each EEG data time series to produce a set of noise reduced EEG data time series;
(v) Detect the steady-state responses in each noise-reduced EEG data time series wherein a steady-state response is recognized at the modulation frequency specific to the modality stimulus that evoked the response; and,
(vi) Compare the amplitudes of the detected responses to normative values matched for age and sex (alternatively the comparison can be done within the subject 60 if modality stimuli are presented to both the left and right sides of the body of the subject 60).

Portable Objective Multi-modality Test Apparatus

Figure 13:
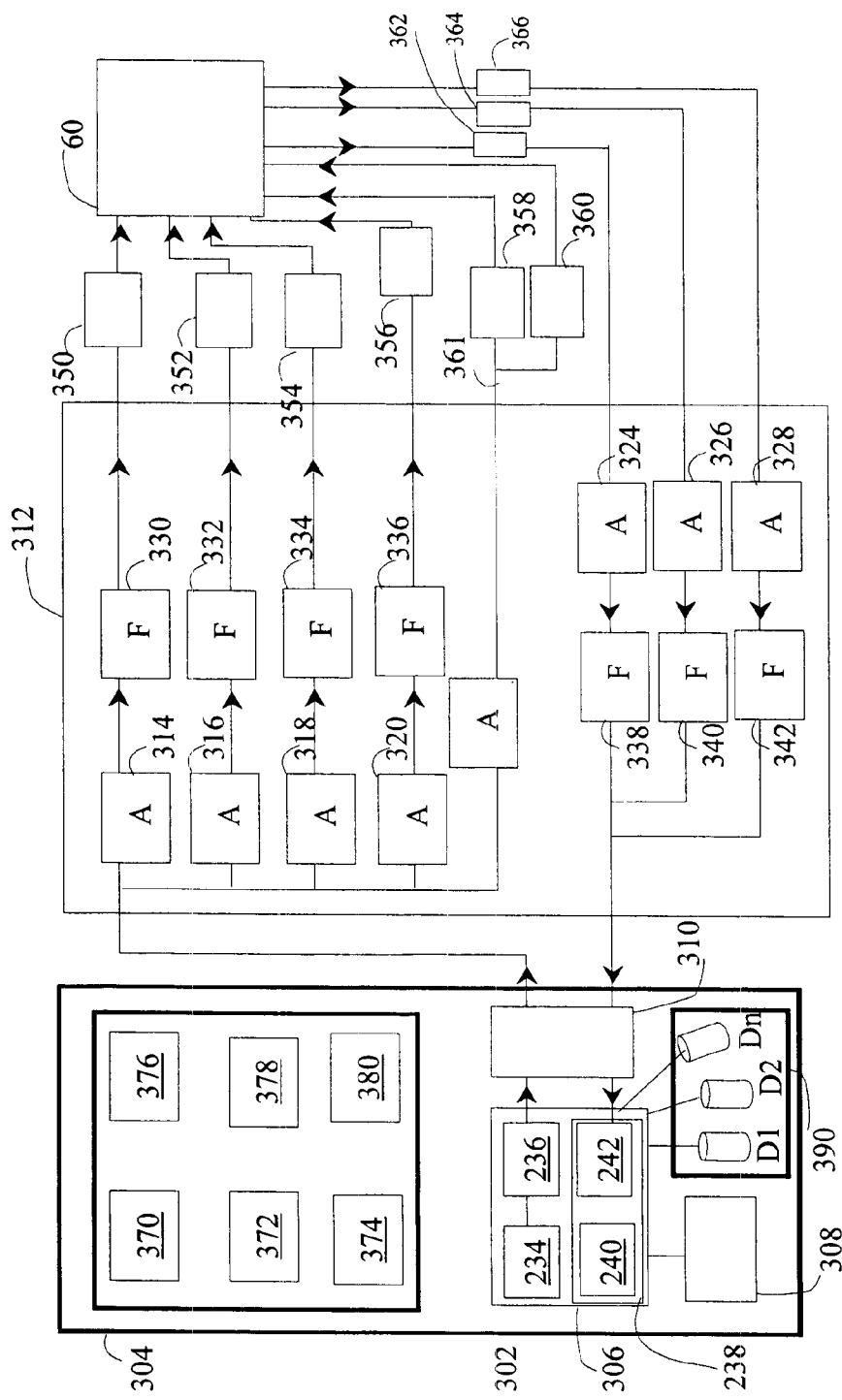
FIG. 13 is a schematic of a portable version of the objective audiometric test apparatus which is also adapted to perform multi-modality testing.

The present invention further comprises a portable objective multi-modality test apparatus 300 as shown in FIG. 13. The portable objective multi-modality test apparatus 300 is similar to the objective multi-modality test apparatus 200 that was shown in FIG. 12 and therefore comprises many of the same components. The portable objective multi-modality test apparatus 300 comprises a laptop computer 302 which has a screen 304, a software program 306, a storage device 308, a master database 390 comprising a plurality of databases D1 to Dn and a PCMCIA data communication card 310. The software program 306 comprises the signal creator 234, the modulator 236 and the analysis module 238 including the noise reduction module 240 and the detection module 242. The objective multi-modality test apparatus 300 further comprises a control box 312 having amplifiers 314, 316, 318, 320, 322, 324, 326 and 328, filters 330, 332, 334, 336, 338, 340 and 342, transducers 350, 352, 354, 356, 358 and 360 and sensors 362, 364 and 366.

The portable objective multi-modality test apparatus 300 operates in much the same manner as the objective multi-modality test apparatus 200 except that the apparatus is based on the laptop 302 and the control box 312. Alternatively, a palmtop or other portable computing device may be used. On the screen 304 there are various graphical user interfaces (GUI) windows that are implemented by the software program 306. There is a Load protocol window 370, a View Stimuli window 372, a View EEG window 374, a data acquisition window 376, a continue acquisition window 378 and a process data window 380. These GUI windows allow a user to operate the portable objective multi-modality test apparatus 300 and perform various tests on the subject 60.

The PCMCIA data communication card 310, which may be a National Instrument DAQCard-6062e card, enables functional communication and data transfer between the laptop 302 and the control box 312. The PCMCIA data communication card 310 provides test signals to the control box 312 and receives the recorded EEG data. Other communication systems may also be used to support data transfer between the components of the system provided that they can support the necessary data transfer rates.

The control box 312 contains two audio amplifiers 314 and 316 which amplify the test signals, provided by the PCMCIA data communication card 310, and provide the test signals to two transducers 350 and 352 which transduce the test signals into acoustic stimuli and present the acoustic stimuli to the subject 60. The laptop 302 controls the intensity of the acoustic stimulus via the gain of the audio amplifiers 314 and 316. Alternatively, eight or more audio amplifiers may be contained in the control box 312 in order to permit separate intensity control of test signals contained within a multiple SSAEP stimulus that may be presented to the subject 60. The output of the audio amplifiers 314 and 316 are then sent to filters 330 and 332 to remove any digitization noise or artifacts in the test signals. The filters 330 and 332 may also be used to introduce pass band masking signals into the test signals. In a like manner, the control box 312 further comprises other amplifiers 318 and 320 and filters 334 and 336 that manipulate the test signals before they are transduced into visual and tactile stimuli.

The various test signals are then transduced by the transducers 350, 352, 354 and 356. The transducers 352 and 354 may be headphones or insert earphones. The transducers 352 and 354 may also be speakers if the ears are not to be tested separately. The transducer 354 provides the visual stimuli to the subject 60 and may be a strobing light source or goggles that can be placed over the eyes of the subject 60. The transducer 356 provides the tactile stimuli to the subject 60 and may be at least one vibration transducer that is attached to at least one finger of the subject 60. Each stimulus in each modality is modulated at a unique frequency. Each stimulus must also be synchronously initiated and locked to the portable objective multi-modality test apparatus 300 so that the steady-state responses to the multi-modality stimulus can be recognized by their signature modulation frequencies (the steady-state responses occur at the modulation frequency used in the modality stimulus).

To record the steady-state responses to each of the modality stimuli, groups of electrodes 362, 364 and 366 are placed on the scalp of the subject 60 as was previously described for the objective multi-modality test apparatus 200. Multi-modality steady-state testing could also be achieved by using multiple scalp recordings (e.g. using 32 electrode locations over the scalp) or by recording the EEG data with a small number of input data channels (e.g., 3) with specifically located electrodes.

The electrodes 362, 364 and 366 provide sets of EEG time series data to the control box 312. These sets of EEG time series data are then amplified by the amplifiers 324, 326 and 328 and filtered by the filters 338, 340 and 342. Alternatively only one amplifier and one filter may be used. The amplifiers 324, 326 and 328 have gain settings which are under the control of the laptop 302. The filters 338, 340 and 342 may be programmable analog filters for lowpass, highpass, and notch filtering the sets of EEG time series data. These filters 338, 340 and 342 may also be controlled by the laptop 30 (the laptop may also control the other amplifiers and filters within the control box 312). The filtered and amplified sets of EEG time series data are then sent to the PCMCIA data communications card 310 where the sets of EEG time series data are digitized and sent to the analysis module 238. The sets of EEG time series data can then be processed to remove noise, via the noise reduction module 240 and then analyzed for response detection via the detection module 242 as was previously described for the objective multi-modality test apparatus 200.

The portable objective multi-modality test apparatus 300 may further comprise means to enable the adjustment of hearing aid devices which may be worn by the subject 60. In particular, the control box 312 may be adapted to communicate with hearing aid devices 358 and 360. The communication may be via a physical connection such as a ribbon cable 361. Alternatively, in the case of implanted hearing aid devices, the communication may occur via RF telemetry as is used to adjust other implanted biomedical devices (such as implanted stimulators). The portable objective multi-modality test apparatus 300 may then be used to adjust the frequency specific gain settings, the filter slope setting or other relevant settings of the hearing aid devices 358 and 360 as described previously in the method of adjusting hear aids using SSAEP stimuli. The adjustment of the hearing aid devices 358 and 360 may be done by a trained medical professional or may be adjusted automatically by the laptop 302 based upon the pass/fail results of the SSAEP testing procedure.

It should be understood that various modifications can be made to the preferred embodiments described and illustrated herein, without departing from the present invention, the scope of which is defined in the appended claims.

What is claimed is:

1. A method of testing the hearing of a subject, said method comprising the steps of:
   (a) selecting at least one test signal;
   (b) modulating at least one of the amplitude and frequency of said at least one test signal by an exponential modulation signal to produce at least one modulated test signal;
   (c) transducing said at least one modulated test signal to create an acoustic stimulus and presenting said acoustic stimulus to said subject;
   (d) sensing potentials from said subject while substantially simultaneously presenting said acoustic stimulus to said subject; and,
   (e) analyzing said potentials to determine whether said potentials comprise data indicative of the presence of at least one steady-state response to said acoustic stimulus.

2. The method of claim 1, wherein said exponential modulation signal comprises a sinusoidal signal having an exponent which is greater than 1 and less than or approximately equal to 4.

3. The method of claim 1, wherein said exponential modulation signal is defined by the formula:

$$y[n]=2*m_a*[(((1+\sin(2*\pi*f_{am}*t*n))/2)^{eam}-0.5)+1]$$

in which:
   y[n] is a time series of data points representing said exponential modulation signal;
   $m_a$ is the AM modulation depth;
   $f_{am}$ is the AM modulation frequency;
   t is the time spacing between said data points;
   n is a given data point; and,
   eam is the exponent of said exponential modulation signal.

4. The method of claim 1, wherein steps (b) and (e) of said method are effected by a software program.

5. A method of testing the hearing of a subject, wherein said method comprises the steps of:
   (a) creating an optimum-vector mixed modulation test signal comprising at least one signal having an amplitude modulated component with a first phase and a frequency modulated component with a second phase wherein said second phase is adjusted relative to said first phase to evoke an increased response from said subject;
   (b) transducing said test signal to create an acoustic stimulus and presenting said acoustic stimulus to said subject;
   (c) sensing potentials from said subject while substantially simultaneously presenting said acoustic stimulus to said subject; and,
   (d) analyzing said potentials to determine whether said potentials comprise data indicative of the presence of at least one steady-state response to said acoustic stimulus.

6. The method of claim 5, wherein said method further comprises creating a database of normative optimal phase difference data correlated to subject characteristics and stimulus characteristics.

7. The method of claim 5, wherein the method further comprising using said database of normative phase difference data to adjust said second phase relative to said first phase.

8. A method of testing the hearing of a subject, wherein said method comprises the steps of:
 (a) creating a test signal comprising at least one independent amplitude modulated and frequency modulated signal having an amplitude modulated component and a frequency modulated component, wherein said amplitude modulated component comprises a first modulation frequency and a first carrier frequency and said frequency modulated component comprises a second modulation frequency and a second carrier frequency wherein said first modulation frequency is substantially different from said second modulation frequency and said first carrier frequency is substantially similar to said second carrier frequency;
 (b) transducing said test signal to create an acoustic stimulus and presenting said acoustic stimulus to said subject;
 (c) sensing potentials from said subject while substantially simultaneously presenting said acoustic stimulus to said subject; and,
 (d) analyzing said potentials to determine whether said potentials comprise data indicative of a steady-state response to each amplitude modulated component and a steady-state response to each frequency modulated component.

9. An apparatus for testing the hearing of a subject, wherein said apparatus comprises:
 (a) a signal creator adapted to create a test signal comprising at least one combined amplitude modulated and frequency modulated signal having an amplitude modulated component with a first phase and a frequency modulated component with a second phase wherein said signal creator comprises means for adjusting said second phase relative to said first phase;
 (b) a transducer electrically coupled to said processor and adapted to transduce said test signal to create an acoustic stimulus and present said acoustic stimulus to said subject;
 (c) a sensor adapted to sense potentials from said subject while said acoustic stimulus is substantially simultaneously presented to said subject; and,
 (d) a processor electrically coupled to said sensor and adapted to receive said potentials and analyze said potentials to determine if said potentials comprise data indicative of at least one response to said acoustic stimulus.

10. The apparatus of claim 9, wherein said apparatus further comprises a database of normative phase differences data correlated to subject characteristics and stimulus characteristics.

11. The apparatus of claim 9, wherein said processor is further adapted to create a second test signal comprising at least one independent amplitude modulated and frequency modulated signal.

12. A method of analyzing potentials to determine whether said potentials comprise data indicative of the presence of at least one steady-state response to a steady-state evoked potential stimulus, wherein said method comprises the steps of:
 (a) presenting an evoked potential stimulus to a subject;
 (b) sensing potentials from said subject while substantially simultaneously presenting said stimulus to said subject to obtain a plurality of data points;
 (c) transforming said plurality of data points into a second plurality of data points;
 (d) biasing said second plurality of data points with an expected phase value to obtain a plurality of biased data points; and,
 (e) applying a statistical test to said plurality of biased data points to detect said response.

13. The method of claim 12, wherein effecting steps (c) and (d) comprises the steps of:
 (f) forming a plurality of sweeps from said plurality of data points;
 (g) averaging said plurality of sweeps to obtain a plurality of averaged data points;
 (h) calculating a plurality of Fourier components for said plurality of averaged data points;
 (i) calculating the amplitude ($a_i$) and phase ($\theta_i$) for said plurality of Fourier components;
 (j) biasing said amplitudes ($a_i$) to obtain biased data points ($p_i$) according to the formula:

$$p_i = a_i * \cos(\theta_i - \theta_e)$$

wherein $\theta_e$ is said expected phase value.

14. The method of claim 12, wherein effecting step (e) comprises the steps of:
 (k) calculating upper confidence limits using a one tailed Student t-test on biased amplitudes which represent noise in the vicinity of Fourier components where said response should occur; and,
 (l) comparing biased amplitudes of Fourier components where said response should occur to said upper confidence limits to determine if said biased amplitudes are larger than said upper confidence limit.

15. The method of claim 12, wherein said expected phase value is obtained from a database of normative expected phase values correlated to subject characteristics and stimulus characteristics.

16. The method of claim 12, wherein said expected phase value is obtained from previous testing on said subject using stimuli having a higher intensity.

17. The method of claim 12, wherein said stimulus contains other components for which responses have been detected and said expected phase value is obtained from extrapolation of said phase values for said responses which have already been detected.

18. A method of detecting a response to an evoked potential stimulus, wherein said method comprises the steps of:
 (a) presenting an evoked potential stimulus to a subject;
 (b) sensing potentials from said subject while substantially simultaneously presenting said stimulus to said subject to obtain a plurality of data points; and,
 (c) calculating phase values for said plurality of data points, wherein, a response is detected if an adequate number of said calculated phase values fall within a predetermined phase value range.

19. The method of claim 18, wherein said effecting step (c) further comprises the steps of:
 (d) separating said plurality of data points into epochs;
 (e) calculating a Fourier component for the frequency at which said response should occur for each epoch; and,
 (f) calculating the phase of each Fourier component calculated in step (e).

20. The method of claim 19, wherein said method further comprises the steps of:
   (g) calculating a target phase range;
   (h) calculating the number of said Fourier components that have a phase that is within the target phase range (N); and,
   (i) using binomial analysis with N to determine whether said plurality of data points contain a response.

21. The method of claim 20, wherein said target phase range is calculated based on a database of normative expected phases correlated to subject characteristics and stimulus characteristics.

22. An apparatus for testing the hearing of a subject, wherein said apparatus comprises:
   (a) a signal creator adapted to create a test signal;
   (b) a transducer electrically coupled to said signal creator and adapted to transduce said test signal to create an acoustic stimulus and present said acoustic stimulus to said subject;
   (c) a sensor adapted to sense potentials from said subject while said acoustic stimulus is substantially simultaneously presented to said subject; and,
   (d) a processor electrically coupled to said sensor and adapted to receive said potentials and analyze said potentials to determine if said potentials comprise data indicative of at least one response to said acoustic stimulus;
   wherein said analysis involves biasing said potentials based on an expected phase value.

23. The apparatus of claim 22, wherein said apparatus further comprises a database of expected phase value data correlated to subject characteristics and stimulus characteristics.

24. A method of noise reduction for a plurality of data points which are obtained during steady-state evoked potential testing, wherein said plurality of data points comprise at least one signal and noise and wherein said method comprises the steps of:
   (a) obtaining said plurality of data points;
   (b) separating said plurality of data points into a plurality of epochs; and,
   (c) applying an adaptive noise reduction method to each epoch.

25. The method of claim 24, wherein said adaptive noise reduction method comprises effecting sample weighted averaging wherein weights are calculated based on the variance of noise, wherein the frequency of the noise is in close proximity to the frequency of the signal.

26. The method of claim 25, wherein said sample weighted averaging is effected according to the steps of:
   (d) forming a plurality of sweeps by concatenating the epochs together;
   (e) filtering each sweep to obtain a plurality of filtered sweeps;
   (f) aligning each sweep to form a first matrix in which the sweeps are the rows of the matrix and the epochs within the plurality of sweeps are the columns of the matrix and aligning each filtered sweep in a similar fashion to form a filtered matrix which is used to calculate weights;
   (g) calculating the variance of each epoch in the filtered matrix to obtain a noise variance estimate for each epoch in the filtered matrix;
   (h) normalizing the noise variance estimate for each epoch in the filtered matrix by dividing the noise variance estimate for each epoch in the filtered matrix by the sum of all noise variance estimates for the epochs along the column of the filtered matrix which contains the epoch to obtain a normalized noise variance estimate for each epoch;
   (i) inverting each normalized noise variance estimate to obtain a weight for each epoch and multiplying each corresponding epoch in the first matrix by its respective weight to obtain a plurality of weighted epochs; and,
   (j) summing all of the weighted epochs in the first matrix along the columns of the first matrix to obtain a signal estimate.

27. The method of claim 26, wherein filtering comprises using a bandpass filter having a passband region which is local to the frequency region where the at least one signal resides such that the calculated weights are based on the frequency region local to the frequency region where the at least one signal resides.

28. A method of objectively testing the hearing of a subject, wherein said method comprises the steps of:
   (a) selecting an auditory test;
   (b) creating an appropriate test signal comprising at least one component for said auditory test;
   (c) transducing said test signal to create a stimulus and presenting said stimulus to said subject;
   (d) sensing potentials from said subject while substantially simultaneously presenting said stimulus to said subject; and,
   (e) analyzing said potentials to detect at least one response.

29. The method of claim 28, wherein said auditory test is a latency test which comprises calculating a latency value for a detected response and comparing said latency value to a database of normative latency values to obtain an indication of the normal/abnormal status of the auditory system of said subject.

30. The method of claim 29, wherein said latency test comprises the steps of:
   (f) calculating an onset phase for each detected response in said sensed potentials;
   (g) calculating a phase delay (P) for each detected response by subtracting each onset phase from 360 degrees;
   (h) calculating a latency value (L) for each detected response according to the following formula:

$$L=1000*(P+N*360)/(360*f_m)$$

where N is the number of cycles that have occurred in the stimulus before each detected response to a respective component of said stimulus occurs and $f_m$ is the frequency of said detected response; and,
   (i) comparing each latency value to a database of normative latency values to obtain an indication of the normal/abnormal status of the auditory system of said subject.

31. The method of claim 30, wherein N is approximately 1 and fm is in the range of approximately 75 to 100 Hz or in the range of approximately 150 to 190 Hz.

32. The method of claim 29, wherein said latency test further comprises the steps of:
   (j) calculating a first latency value for a first detected response and calculating a second latency value for a second detected response;
   (k) finding the difference between said first latency value and said second latency value to obtain a differential latency value; and, (l) comparing said differential latency value to a database of normative differential latency values to obtain an indication of the status of the auditory system of said subject.

33. The method of claim 28, wherein said auditory test is an aided hearing test which comprises the following steps:
(m) fitting said subject with a hearing aid;
(n) performing steps (b) to (e);
(o) adjusting the hearing aid if an inadequate number of responses are detected in step (e); and,
(p) performing steps (n) and (o) until an adequate number of responses have been detected in said potentials.

34. The method of claim 33, wherein said method further comprises effecting step (o) by adjusting the gain of said hearing aid for a frequency region which is substantially similar to the frequency region of a component in said test signal for which a response was not detected.

35. The method of claim 28, wherein said auditory test is an AM/FM discrimination test and said test signal comprises at least one independent amplitude modulation and frequency modulation signal, wherein, said AM/FM discrimination test comprises the steps of:
(q) performing steps (b) to (e);
(r) calculating a response ratio according to the number of detected responses divided by the total number of responses which could have occurred in response to said stimulus; and,
(s) estimating a word recognition score correlated to said response ratio.

36. The method of claim 35, wherein said test signal further comprises noise masking.

37. The method of claim 28, wherein said auditory test is an AM/FM discrimination test and said test signal comprises an amplitude modulated component and a frequency modulated component, wherein, said AM/FM discrimination test comprises the steps of:
(t) performing steps (b) to (e);
(u) calculating a first amplitude of a response to said frequency modulated component;
(v) calculating a second amplitude of a response to said amplitude modulated component;
(x) calculating an amplitude ratio by dividing said first amplitude by said second amplitude; and,
(y) comparing said amplitude ratio to a database of normative amplitude ratios to obtain an indication of the status of the auditory system of said subject.

38. The method of claim 37, wherein said test signal comprises a plurality of pairs of amplitude modulated components and frequency modulated components and the method further comprises carrying out steps (u) to (y) for each of said pairs.

39. The method of claim 28, wherein said auditory test is a depth sensitivity test and said test signal comprises one or more amplitude modulated components having a modulation depth or one or more frequency modulated components having a modulation depth, wherein, said depth sensitivity test comprises the steps of:
(z) carrying out steps (b) to (e);
(aa) obtaining an estimate of response amplitude for each detected response; and,
(bb) comparing each estimated response amplitude with a database of normative response amplitudes to obtain an indication of the status of the auditory system of said subject.

40. The method of claim 39, wherein said depth sensitivity test further comprises the steps of:
(cc) detecting responses to test signals comprising a first modulated component having a first modulation depth and a second modulated component having a second modulation depth, wherein said modulation depths are different;
(dd) analyzing said detected responses to obtain an estimate of a first response amplitude for a detected response to said first modulated component and a second response amplitude for a detected response to said second modulated component;
(ee) calculating a response amplitude ratio from said first response amplitude and said second response amplitude; and,
(ff) comparing said response amplitude ratio with a database of normative response amplitude ratios to obtain an indication of the status of the auditory system of said subject.

41. The method of claim 28, wherein said auditory test is a rate sensitivity test which comprises the following steps:
(gg) creating a set of modulation frequencies comprising at least two modulation frequencies;
(hh) creating a set of test signals wherein each test signal comprises at least one amplitude modulated component having a unique modulation frequency chosen from said set of modulation frequencies;
(ii) carrying out steps (c) and (d) for each test signal in said set of test signals;
(jj) analyzing said set of potentials to detect a response for each amplitude modulated component in said set of test signals and estimating a response amplitude for each detected response;
(kk) calculating a rate sensitivity value based on said estimated response amplitudes; and,
(ll) comparing said rate sensitivity value to a database of normative rate sensitivity values to obtain an indication of the status of the auditory system of said subject.

42. The method of claim 41, wherein said rate sensitivity value is the slope of the line resulting from a plot of estimated response amplitude for each amplitude modulated component versus modulation frequency for each amplitude modulated component.

43. The method of claim 28, wherein said auditory test is a supra-threshold test comprising an intensity limen test and said test signal comprises an amplitude modulated component having a modulation depth of approximately 100%, wherein said intensity limen test comprises the steps of:
(mm) performing steady state evoked potential testing while minimizing the modulation depth of the test signal upon each detected response to determine a minimum modulation depth at which a response is detected; and,
(nn) comparing said minimum modulation depth with a database of normative minimum modulation depths to obtain an indication of the status of the auditory system of said subject.

44. The method of claim 43, wherein said supra-threshold test further comprises a frequency limen test and said test signal comprises an amplitude modulated component having a frequency modulation depth, wherein, said frequency limen test comprises the steps of:
(oo) determining a minimum modulation depth at which a response is detected; and,
(pp) comparing said minimum modulation depth with a database of normative minimum modulation depths to obtain an indication of the status of the auditory system of said subject.

45. The method of claim 28, wherein said auditory test is an auditory threshold test and said test signal comprises two or more combined amplitude modulation and frequency modulation signals having carrier frequencies which are separated by more than one-half octave, wherein, each combined amplitude modulation and frequency modulation signal has a frequency modulated component and an amplitude modulated component and the phase of the frequency modulated component is adjusted relative to the phase of the amplitude modulated component, wherein said auditory threshold test comprises the step of:

(qq) carrying out steps (c) to (e) to determine a minimal stimulus intensity for which a response is detected for each combined amplitude modulation and frequency modulation signal.

46. The method of claim 45, wherein the envelope of each combined amplitude modulation and frequency modulation signal is modulated by an exponential modulation signal.

47. The method of claim 45, wherein said auditory threshold test is conducted for a maximum time limit which is adjusted depending on the amount of noise in said potentials.

48. The method of claim 45, wherein said auditory threshold test comprises upwardly adjusting the intensities of components in said stimulus which tend to evoke responses having smaller amplitudes, so that all components in said stimulus evoke responses having similar amplitudes.

49. The method of claim 45, wherein step (e) comprises the step of:

(rr) reducing noise in said potentials to obtain reduced noise potentials by employing sample weighted averaging.

50. The method of claim 45, wherein step (e) comprises the step of:

(ss) performing a phase weighted t-test on said potentials to determine whether said potentials comprise data indicative of at least one response to said stimulus.

51. The method of claim 45, wherein step (e) comprises the step of:

(tt) performing a modified Rayleigh test of circular uniformity (MRC) on said potentials to determine whether said potentials comprise data indicative of at least one response to said stimulus.

52. The method of claim 45, wherein adjusting said intensity of one of said components comprises using the Stimulus Flux method which comprises creating another waveform of appropriate phase and amplitude, which when added to said test signal, results in the desired adjustment of said intensity of one of said components.

53. An apparatus for objectively testing the hearing of a subject, wherein said apparatus comprises:

(a) a selector adapted for selecting an auditory test to perform on said subject;

(b) a signal creator electrically coupled to said selector and adapted to create an appropriate test signal comprising at least one component for said test;

(c) a transducer electrically coupled to said signal creator and adapted to transduce said test signal to create an acoustic stimulus and present said acoustic stimulus to said subject;

(d) a sensor adapted to sense potentials from said subject while said acoustic stimulus is substantially simultaneously presented to said subject;

(e) a processor electrically coupled to said sensor and adapted to receive said potentials and analyze said potentials to determine if said potentials comprise data indicative of at least one response to said acoustic stimulus; and, (f) a programmable hearing aid coupled to said processor, wherein, said programmable hearing aid comprises a plurality of programmable gain factors for different frequency regions and at least one programmable filter slope.

54. A method of testing at least two senses of a subject, wherein said method comprises the steps of:

(a) selecting a first steady-state test signal to test a first sensory modality;

(b) transducing said first steady-state test signal to create a first stimulus and presenting said first stimulus to said subject;

(c) selecting a second steady-state test signal to test a second sensory modality;

(d) transducing said second steady-state test signal to create a second stimulus and presenting said second stimulus to said subject;

(e) sensing potentials while substantially simultaneously presenting both stimuli to said subject; and, (f) analyzing said potentials to determine whether said potentials comprise data indicative of at least one steady-state response to said stimuli.

55. The method of claim 54, wherein said steady-state test signals comprise an auditory signal, a visual signal and a tactile signal.

56. The method of claim 54, wherein said method further comprises ensuring that all modulation frequencies in the stimuli are not integer multiples of one another.

57. An apparatus for testing at least two senses of a subject, wherein said apparatus comprises:

(a) a signal creator adapted to create a first steady-state test signal and a second steady-state test signal;

(b) a first transducer electrically coupled to said selector and adapted to transduce said first test signal to create a first stimulus and present said first stimulus to said subject;

(c) a second transducer electrically coupled to said selector and adapted to transduce said second test signal to create a second stimulus and present said second stimulus to said subject;

(d) a first sensor adapted to sense first potentials from said subject while said first stimulus is substantially simultaneously presented to said subject;

(e) a second sensor adapted to sense second potentials from said subject while said second stimulus is substantially simultaneously presented to said subject;

(f) a processor electrically coupled to said first sensor and adapted to receive said first potentials and analyze said first potentials to determine if said first potentials comprise data indicative of at least one response to said first stimulus; and, (g) the processor, electrically coupled to said second sensor and adapted to receive said second potentials and analyze said second potentials to determine if said second potentials comprise data indicative of at least one response to said second stimulus, wherein, each stimulus is presented substantially simultaneously.

* * * * *